US010889628B2

(12) United States Patent
Gross et al.

(10) Patent No.: US 10,889,628 B2
(45) Date of Patent: Jan. 12, 2021

(54) OPTOGENETIC INHIBITION OF OVERACTIVE NEURONAL ACTIVITY

(71) Applicant: Emory University, Atlanta, GA (US)

(72) Inventors: Robert E. Gross, Decatur, GA (US); Nealen G. Laxpati, Atlanta, GA (US); Jack Tung, Duluth, GA (US); Ken Berglund, Kennesaw, GA (US)

(73) Assignee: Emory University, Atlanta, GA (US)

( * ) Notice: Subject to any disclaimer, the term of this patent is extended or adjusted under 35 U.S.C. 154(b) by 338 days.

(21) Appl. No.: 15/893,884

(22) Filed: Feb. 12, 2018

(65) Prior Publication Data
US 2018/0237491 A1    Aug. 23, 2018

Related U.S. Application Data

(62) Division of application No. 14/529,539, filed on Oct. 31, 2014, now Pat. No. 9,926,359.

(60) Provisional application No. 61/908,964, filed on Nov. 26, 2013.

(51) Int. Cl.
| C12N 15/85 | (2006.01) |
| C07K 14/705 | (2006.01) |
| C12N 9/02 | (2006.01) |
| A61K 31/4985 | (2006.01) |

(52) U.S. Cl.
CPC .......... *C07K 14/705* (2013.01); *C12N 9/0069* (2013.01); *A61K 31/4985* (2013.01); *C07K 2319/00* (2013.01); *C07K 2319/60* (2013.01); *C12Y 113/12005* (2013.01)

(58) Field of Classification Search
None
See application file for complete search history.

(56) References Cited

U.S. PATENT DOCUMENTS

| 9,926,359 | B2 | 3/2018 | Gross |
| 2010/0145418 | A1 | 6/2010 | Zhang |
| 2015/0072394 | A1 | 3/2015 | Deisseroth |
| 2016/0036875 | A1 | 2/2016 | Lundmark |

FOREIGN PATENT DOCUMENTS

| JP | 2011067190 | 4/2011 |
| WO | 2010011404 | 1/2010 |
| WO | 2010056970 | 5/2010 |
| WO | 2011005978 | 1/2011 |
| WO | 2013090356 | 6/2013 |

OTHER PUBLICATIONS

Acharya et al., Automated EEG analysis of epilepsy: A review, Knowledge-Based Systems 45 (2013) 147-165.
Badea et al. Calcium imaging of epileptiform events with single-cell resolution, J Neurobiol, 2001; 48: 215-227.
Bergland et al. Lumigenetics: Multimodal control of neural circuits by combining optogenetics with bioluminescence, Soc for Neurosci Abstr, 2011.
Berglund et al.Light-Emitting Channelrhodopsins for Combined Optogenetic and Chemical-Genetic Control of Neurons, PLOS ONE, 2013; 8(3): e59759.
Contag, In Vivo Pathology: Seeing with Molecular Specificity and Cellular Resolution in the Living Body, Annu. Rev. Pathol. Mech. Dis., 2007; 2: 277-305.
Desai et al. Deep brain stimulation macroelectrodes compared to multiple microelectrodes in rat hippocampus, Frontiers in Neuroengineering, 2014; 7(16): 1-8.
Drobac et al. Calcium imaging in single neurons from brain slices using bioluminescent reporters, J Neurosci Res., 2010; 88: 695-71.
Inouye et al. The Use of Renilla Luciferase, Oplophorus Luciferase, and Apoaequorin as Bioluminescent Reporter Protein in the Presence of Coelenterazine Analogues as Substrate, Biochemical and Biophysical Research Communications 233,349-353 (1997).
Laxpati et al. Optogenetic Activation of Hippocampal Pyramidal Cells is Highly Dependent on the Parameters of Stimulation, Soc for Neurosci Abstr, 2011.
Laxpati et al. Deep Brain Stimulation for the Treatment of Epilepsy: Circuits, Targets, and Trials, Neurotherapeutics, 2014; 11: 508-526.
Rodgers et al. Progressive, Seizure-Like, Spike-Wave Discharges Are Common in Both Injured and Uninjured Sprague-Dawley Rats: Implications for the Fluid Percussion Injury Model of Post-Traumatic Epilepsy, The Journal of Neuroscience, 35(24):9194-9204.
Saito et al. Luminescent proteins for high-speed single-cell and whole-body imaging, Nat. Commun., 2012; 3: 1262.
Tung et al. Optogenetic inhibition using a genetically encoded bioluminescent light source, Society for Neuroscience Abstract Viewer and Itinerary Planner, 2013; vol. 43.
Tung et al. Inhibitory luminopsins: genetically encoded bioluminescent opsins for versatile, scalable, and hardware independent optogenetic inhibition, Scientific Reports, 2015; 5:14366.

(Continued)

*Primary Examiner* — Maria G Leavitt
(74) *Attorney, Agent, or Firm* — Emory Patent Group

(57) ABSTRACT

This disclosure relates to recombinant proteins, vectors, and methods of treating neurological conditions by exposing neurons to an opsin and luciferase in the presence of a luciferin. In certain embodiments, the disclosure relates to treating or preventing epilepsy or seizures comprising administering an effective amount of a vector that encodes an opsin and luciferase in combination with a luciferin to a subject in need thereof.

14 Claims, 5 Drawing Sheets

Specification includes a Sequence Listing.

(56) References Cited

OTHER PUBLICATIONS

Verhaegen et al. Recombinant Gaussia Luciferase. Overexpression, Purification, and Analytical Application of a Bioluminescent Reporter for DNA Hybridization, Anal. Chem., 2002; 74: 4378-4385.
Willie et al. Real-Time Magnetic Resonance-Guided Stereotactic Laser Amygdalohippocampotomy for Mesial Temporal Lobe Epilepsy, Neurosurgery, 2014; 74: 569-585.
Zhang et al. Multimodal fast optical interrogation of neural circuitry, Nature, 2007; 446: 633-639.
Zhao et al. Improved expression of halorhodopsin for light-induced silencing of neuronal activity, Brain Cell Biol., 2008; 36(1-4): 141-154.

SEQUENCE LISTING

```
<160> NUMBER OF SEQ ID NOS: 18

<210> SEQ ID NO 1
<211> LENGTH: 561
<212> TYPE: PRT
<213> ORGANISM: Artificial
<220> FEATURE:
<223> OTHER INFORMATION: Synthetic construct

<400> SEQUENCE: 1

Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Met Tyr Gly Ser Arg Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95
```

-continued

Val Thr Thr Tyr Glu Asp Gly Gly Val Leu Thr Ala Thr Gln Asp Thr
            100             105             110

Ser Leu Gln Asp Gly Cys Leu Ile Tyr Asn Val Lys Ile Arg Gly Val
        115             120             125

Asn Phe Pro Ser Asn Gly Pro Val Met Gln Lys Lys Thr Leu Gly Trp
    130             135             140

Glu Ala Asn Thr Glu Met Leu Tyr Pro Ala Asp Gly Gly Leu Glu Gly
145             150             155             160

Arg Ser Asp Met Ala Leu Lys Leu Val Gly Gly His Leu Ile Cys
                165             170             175

Asn Phe Lys Thr Thr Tyr Arg Ser Lys Lys Pro Ala Lys Asn Leu Lys
            180             185             190

Met Pro Gly Val Tyr Tyr Val Asp His Arg Leu Glu Arg Ile Lys Glu
        195             200             205

Ala Asp Lys Glu Thr Tyr Val Glu Gln His Glu Val Ala Val Ala Arg
    210             215             220

Tyr Cys Asp Leu Pro Ser Lys Leu Gly His Lys Leu Asn Ser Gly Leu
225             230             235             240

Arg Ser Asp Ile Gly Pro Ser Arg Ala Thr Met Ala Ser Lys Val Tyr
                245             250             255

Asp Pro Glu Gln Arg Lys Arg Met Ile Thr Gly Pro Gln Trp Trp Ala
            260             265             270

Arg Cys Lys Gln Met Asn Val Leu Asp Ser Phe Ile Asn Tyr Tyr Asp
        275             280             285

Ser Glu Lys His Ala Glu Asn Ala Val Ile Phe Leu His Gly Asn Ala
    290             295             300

Thr Ser Ser Tyr Leu Trp Arg His Val Val Pro His Ile Glu Pro Val
305             310             315             320

Ala Arg Cys Ile Ile Pro Asp Leu Ile Gly Met Gly Lys Ser Gly Lys
                325             330             335

Ser Gly Asn Gly Ser Tyr Arg Leu Leu Asp His Tyr Lys Tyr Leu Thr
            340             345             350

Ala Trp Phe Glu Leu Leu Asn Leu Pro Lys Lys Ile Ile Phe Val Gly
        355             360             365

His Asp Trp Gly Ser Ala Leu Ala Phe His Tyr Ala Tyr Glu His Gln
    370             375             380

Asp Arg Ile Lys Ala Ile Val His Met Glu Ser Val Val Asp Val Ile
385             390             395             400

Glu Ser Trp Met Gly Trp Pro Asp Ile Glu Glu Glu Leu Ala Leu Ile
                405             410             415

Lys Ser Glu Glu Gly Glu Lys Met Val Leu Glu Asn Asn Phe Phe Val
            420             425             430

Glu Thr Leu Leu Pro Ser Lys Ile Met Arg Lys Leu Glu Pro Glu Glu
        435             440             445

Phe Ala Ala Tyr Leu Glu Pro Phe Lys Glu Lys Gly Glu Val Arg Arg
    450             455             460

Pro Thr Leu Ser Trp Pro Arg Glu Ile Pro Leu Val Lys Gly Gly Lys
465             470             475             480

Pro Asp Val Val Gln Ile Val Arg Asn Tyr Asn Ala Tyr Leu Arg Ala
                485             490             495

Ser Asp Asp Leu Pro Lys Leu Phe Ile Glu Ser Asp Pro Gly Phe Phe
            500             505             510

Ser Asn Ala Ile Val Glu Gly Ala Lys Lys Phe Pro Asn Thr Glu Phe

|     |     |     |     |     |     |     |     |     |     |     |     |
| --- | --- | --- | --- | --- | --- | --- | --- | --- | --- | --- | --- |
|     |     | 515 |     |     |     | 520 |     |     |     | 525 |     |
| Val | Lys | Val | Lys | Gly | Leu | His | Phe | Leu | Gln | Glu | Asp | Ala | Pro | Asp | Glu |
|     |     | 530 |     |     |     | 535 |     |     |     | 540 |     |
| Met | Gly | Lys | Tyr | Ile | Lys | Ser | Phe | Val | Glu | Arg | Val | Leu | Lys | Asn | Glu |
| 545 |     |     |     |     | 550 |     |     |     |     | 555 |     |     |     |     | 560 |
| Gln |

<210> SEQ ID NO 2
<211> LENGTH: 1683
<212> TYPE: DNA
<213> ORGANISM: Artificial
<220> FEATURE:
<223> OTHER INFORMATION: Synthetic construct

<400> SEQUENCE: 2

```
atggtgtcta agggcgaaga gctgattaag gagaacatgc acatgaagct gtacatggag      60
ggcaccgtga acaaccacca cttcaagtgc acatccgagg gcgaaggcaa gccctacgag     120
ggcacccaga ccatgagaat caaggtggtc gagggcggcc ctctcccctt cgccttcgac     180
atcctggcta ccagcttcat gtacggcagc agaaccttca tcaaccacac ccagggcatc     240
cccgacttct ttaagcagtc cttccctgag ggcttcacat gggagagagt caccacatac     300
gaagacgggg gcgtgctgac cgctacccag gacaccagcc tccaggacgg ctgcctcatc     360
tacaacgtca gatcagagg ggtgaacttc ccatccaacg ccctgtgat gcagaagaaa      420
acactcggct gggaggccaa caccgagatg ctgtaccccg ctgacggcgg cctggaaggc     480
agaagcgaca tggccctgaa gctcgtgggc gggggccacc tgatctgcaa cttcaagacc     540
acatacagat ccaagaaacc cgctaagaac ctcaagatgc ccggcgtcta ctatgtggac     600
cacagactgg aaagaatcaa ggaggccgac aaagagacct acgtcgagca gcacgaggtg     660
gctgtggcca gatactgcga cctccctagc aaactggggc acaaacttaa ttccggactc     720
agatctgata tcgggccctc tagagccacc atggcttcca aggtgtacga ccccgagcaa     780
cgcaaacgca tgatcactgg gcctcagtgg tgggctcgct gcaagcaaat gaacgtgctg     840
gactccttca tcaactacta tgattccgag aagcacgccg agaacgccgt gattttctg     900
catggtaacg ctacctccag ctacctgtgg aggcacgtcg tgcctcacat cgagcccgtg     960
gctagatgca tcatccctga tctgatcgga atgggtaagt ccggcaagag cgggaatggc    1020
tcatatcgcc tcctggatca ctacaagtac ctcaccgctt ggttcgagct gctgaacctt    1080
ccaaagaaaa tcatctttgt gggccacgac tggggagcg ctctggcctt tcactacgcc    1140
tacgagcacc aagacaggat caaggccatc gtccatatgg agagtgtcgt ggacgtgatc    1200
gagtcctgga tggggtggcc tgacatcgag gaggagctgg ccctgatcaa gagcgaagag    1260
ggcgagaaaa tggtgcttga gaataacttc ttcgtcgaga ccctgttgcc aagcaagatc    1320
atgcggaaac tggagcctga ggagttcgct gcctacctgg agccattcaa ggagaagggc    1380
gaggttagac ggcctaccct ctcctggcct cgcgagatcc ctctcgttaa gggaggcaag    1440
cccgacgtcg tccagattgt ccgcaactac aacgcctacc ttcgggccag cgacgatctg    1500
cctaagctgt tcatcgagtc cgaccctggg ttcttttcca acgctattgt cgagggagct    1560
aagaagttcc ctaacaccga gttcgtgaag gtgaagggcc tccacttcct ccaggaggac    1620
gctccagatg aaatgggtaa gtacatcaag agcttcgtgg agcgcgtgct gaagaacgag    1680
cag                                                                1683
```

<210> SEQ ID NO 3
<211> LENGTH: 2568
<212> TYPE: DNA
<213> ORGANISM: Artificial
<220> FEATURE:
<223> OTHER INFORMATION: Synthetic construct

<400> SEQUENCE: 3

| | | | | | |
|---|---|---|---|---|---|
| atgacagaga | ccctgcctcc | cgtgaccgag | agtgccgtgg | cccttcaagc | cgaggttacc | 60 |
| caaagggagt | tgttcgagtt | cgtgctgaac | gacccttgc | ttgcaagcag | tctctatatc | 120 |
| aacatcgcac | ttgcaggact | gagtatactg | ctgttcgttt | ttatgacccg | aggactcgat | 180 |
| gatccacggg | caaaacttat | tgctgtgtca | accatccttg | tgcctgtcgt | cagcattgcc | 240 |
| tcctacactg | gattggcgag | cggcctgaca | atttccgttc | ttgaaatgcc | agcgggccat | 300 |
| tttgcagaag | gcagctcagt | gatgctggga | ggagaagagg | tagatggtgt | agtcaccatg | 360 |
| tggggacggt | atctcacctg | gcacttttcc | acgcccatga | ttctcctcgc | tctgggtctc | 420 |
| ctggccggaa | gcaatgctac | aaagctcttc | acagctatca | ctttcgatat | cgctatgtgc | 480 |
| gtgactggcc | ttgccgcggc | cctgactacc | tcctcccacc | tcatgagatg | gttctggtac | 540 |
| gctatcagtt | gtgcatgctt | tctggtggtc | ttgtatatcc | tgctggtgga | gtgggcacag | 600 |
| gacgccaaag | ccgcgggaac | cgctgacatg | ttcaataccc | tgaagctgtt | gacagtagtg | 660 |
| atgtggctgg | ggtatccaat | tgtgtgggct | cttggagtcg | agggtatcgc | ggtgttgccc | 720 |
| gttggggtga | cgagctgggg | atattctttc | ctggatatcg | tggcaaagta | cattttcgca | 780 |
| ttcttgctcc | tgaactatct | gacgtcaaac | gaatctgtcg | tgtccggcag | cattttggat | 840 |
| gttccatctg | cttctgggac | cccggctgat | gatgcggccg | ctatggtgtc | taagggcgaa | 900 |
| gagctgatta | aggagaacat | gcacatgaag | ctgtacatgg | agggcaccgt | gaacaaccac | 960 |
| cacttcaagt | gcacatccga | gggcgaaggc | aagccctacg | agggcaccca | gaccatgaga | 1020 |
| atcaaggtgg | tcgagggcgg | ccctctcccc | ttcgccttcg | acatcctggc | taccagcttc | 1080 |
| atgtacggca | gcagaacctt | catcaaccac | acccagggca | tccccgactt | ctttaagcag | 1140 |
| tccttccctg | agggcttcac | atgggagaga | gtcaccacat | acgaagacgg | gggcgtgctg | 1200 |
| accgctaccc | aggacaccag | cctccaggac | ggctgcctca | tctacaacgt | caagatcaga | 1260 |
| ggggtgaact | tcccatccaa | cggccctgtg | atgcagaaga | aaacactcgg | ctgggaggcc | 1320 |
| aacaccgaga | tgctgtaccc | cgctgacggc | ggcctggaag | cagaagcga | catggccctg | 1380 |
| aagctcgtgg | gcggggggcca | cctgatctgc | aacttcaaga | ccacatacag | atccaagaaa | 1440 |
| cccgctaaga | acctcaagat | gcccggcgtc | tactatgtgg | accacagact | ggaaagaatc | 1500 |
| aaggaggccg | acaaagagac | ctacgtcgag | cagcacgagg | tggctgtggc | cagatactgc | 1560 |
| gacctcccta | gcaaactggg | gcacaaactt | aattccggac | tcagatctga | tatcgggccc | 1620 |
| tctagagcca | ccatggcttc | caaggtgtac | gaccccgagc | aacgcaaacg | catgatcact | 1680 |
| gggcctcagt | ggtgggctcg | ctgcaagcaa | atgaacgtgc | tggactcctt | catcaactac | 1740 |
| tatgattccg | agaagcacgc | cgagaacgcc | gtgatttttc | tgcatggtaa | cgctacctcc | 1800 |
| agctacctgt | ggaggcacgt | cgtgcctcac | atcgagcccg | tggctagatg | catcatccct | 1860 |
| gatctgatcg | gaatgggtaa | gtccggcaag | agcgggaatg | gctcatatcg | cctcctggat | 1920 |
| cactacaagt | acctcaccgc | ttggttcgag | ctgctgaacc | ttccaaagaa | aatcatcttt | 1980 |
| gtgggccacg | actgggggag | cgctctggcc | tttcactacg | cctacgagca | ccaagacagg | 2040 |
| atcaaggcca | tcgtccatat | ggagagtgtc | gtggacgtga | tcgagtcctg | gatggggtgg | 2100 |

| | |
|---|---:|
| cctgacatcg aggaggagct ggccctgatc aagagcgaag agggcgagaa aatggtgctt | 2160 |
| gagaataact tcttcgtcga gaccctgttg ccaagcaaga tcatgcggaa actggagcct | 2220 |
| gaggagttcg ctgcctacct ggagccattc aaggagaagg gcgaggttag acggcctacc | 2280 |
| ctctcctggc ctcgcgagat ccctctcgtt aagggaggca agcccgacgt cgtccagatt | 2340 |
| gtccgcaact acaacgccta ccttcgggcc agcgacgatc tgcctaagct gttcatcgag | 2400 |
| tccgaccctg ggttcttttc caacgctatt gtcgagggag ctaagaagtt ccctaacacc | 2460 |
| gagttcgtga aggtgaaggg cctccacttc ctccaggagg acgctccaga tgaaatgggt | 2520 |
| aagtacatca agagcttcgt ggagcgcgtg ctgaagaacg agcagtaa | 2568 |

<210> SEQ ID NO 4
<211> LENGTH: 11763
<212> TYPE: DNA
<213> ORGANISM: Artificial
<220> FEATURE:
<223> OTHER INFORMATION: Synthetic construct

<400> SEQUENCE: 4

| | |
|---|---:|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |

```
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggcatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aagggggggat   2460 tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta agggtgcagc ggcctccgcg ccgggttttg gcgcctcccg   2640
cgggcgcccc cctcctcacg gcgagcgctg ccacgtcaga cgaagggcgc aggagcgttc   2700
ctgatccttc cgcccggacg ctcaggacag cggcccgctg ctcataagac tcggccttag   2760
aaccccagta tcagcagaag gacattttag gacgggactt gggtgactct agggcactgg   2820
ttttctttcc agagagcgga acaggcgagg aaaagtagtc ccttctcggc gattctgcgg   2880
agggatctcc gtggggcggt gaacgccgat gattatataa ggacgcgccg ggtgtggcac   2940
agctagttcc gtcgcagccg ggatttgggt cgcggttctt gtttgtggat cgctgtgatc   3000
gtcacttggt gagttgcggg ctgctgggct ggccggggct ttcgtggccg ccgggccgct   3060
cggtgggacg gaagcgtgtg gagagaccgc caagggctgt agtctgggtc cgcgagcaag   3120
gttgccctga actgggggtt ggggggagcg cacaaaatgg cggctgttcc cgagtcttga   3180
atggaagacg cttgtaaggc gggctgtgag gtcgttgaaa caaggtgggg ggcatggtgg   3240
gcggcaagaa cccaaggtct tgaggccttc gctaatgcgg gaaagctctt attcgggtga   3300
gatgggctgg ggcaccatct ggggaccctg acgtgaagtt tgtcactgac tggagaactc   3360
gggtttgtcg tctggttgcg ggggcggcag ttatgcggtg ccgttgggca gtgcacccgt   3420
acctttggga gcgcgcgcct cgtcgtgtcg tgacgtcacc cgttctgttg gcttataatg   3480
cagggtgggg ccacctgccg gtaggtgtgc ggtaggcttt tctccgtcgc aggacgcagg   3540
gttcgggcct agggtaggct ctcctgaatc gacaggcgcc ggacctctgg tgaggggagg   3600
gataagtgag gcgtcagttt ctttggtcgg ttttatgtac ctatcttctt aagtagctga   3660
agctccggtt ttgaactatg cgctcggggt tggcgagtgt gttttgtgaa gttttttagg   3720 cacctttga aatgtaatca tttgggtcaa tatgtaattt tcagtgttag actagtaaag   3780
cttctgcagg tcgactctag aaaattgtcc gctaaattct ggccgttttt ggcttttttg   3840
ttagacagga tccccgggta ccatgacaga gaccctgcct cccgtgaccg agagtgccgt   3900
ggcccttcaa gccgaggtta cccaagggga gttgttcgag ttcgtgctga acgacccttt   3960
```

-continued

```
gcttgcaagc agtctctata tcaacatcgc acttgcagga ctgagtatac tgctgttcgt    4020
ttttatgacc cgaggactcg atgatccacg ggcaaaactt attgctgtgt caaccatcct    4080
tgtgcctgtc gtcagcattg cctcctacac tggattggcg agcggcctga caatttccgt    4140
tcttgaaatg ccagcggcc attttgcaga aggcagctca gtgatgctgg aggagaaga     4200
ggtagatggt gtagtcacca tgtggggacg gtatctcacc tgggcacttt ccacgcccat    4260
gattctcctc gctctgggtc tcctggccgg aagcaatgct acaaagctct tcacagctat    4320
cactttcgat atcgctatgt gcgtgactgg ccttgccgcg ccctgacta cctcctccca    4380
cctcatgaga tggttctggt acgctatcag ttgtgcatgc tttctggtgg tcttgtatat    4440
cctgctggtg gagtgggcac aggacgccaa agccgcggga accgctgaca tgttcaatac    4500
cctgaagctg ttgacagtag tgatgtggct ggggtatcca attgtgtggg ctcttggagt    4560
cgagggtatc gcggtgttgc ccgttggggt gacgagctgg ggatattctt tcctggatat    4620
cgtggcaaag tacattttcg cattcttgct cctgaactat ctgacgtcaa acgaatctgt    4680
cgtgtccggc agcattttgg atgttccatc tgcttctggg accccggctg atgatgcggc    4740
cgctatggtg tctaagggcg aagagctgat taaggagaac atgcacatga agctgtacat    4800
ggagggcacc gtgaacaacc accacttcaa gtgcacatcc gagggcgaag gcaagcccta    4860
cgagggcacc cagaccatga gaatcaaggt ggtcgagggc ggccctctcc ccttcgcctt    4920
cgacatcctg ctaccagct tcatgtacgg cagcagaacc ttcatcaacc acacccaggg    4980
catccccgac ttctttaagc agtccttccc tgagggcttc acatgggaga gagtcaccac    5040
atacgaagac gggggcgtgc tgaccgctac ccaggacacc agcctccagg acggctgcct    5100
catctacaac gtcaagatca gaggggtgaa cttcccatcc aacggccctg tgatgcagaa    5160
gaaaacactc ggctgggagg ccaacaccga gatgctgtac cccgctgacg gcggcctgga    5220
aggcagaagc gacatggccc tgaagctcgt gggcgggggc cacctgatct gcaacttcaa    5280
gaccacatac agatccaaga aacccgctaa gaacctcaag atgcccggcg tctactatgt    5340
ggaccacaga ctggaaagaa tcaaggaggc cgacaaagag acctacgtcg agcagcacga    5400
ggtggctgtg ccagatact gcgacctccc tagcaaactg gggcacaaac ttaattccgg    5460
actcagatct gatatcgggc cctctagagc caccatggct tccaaggtgt acgaccccga    5520
gcaacgcaaa cgcatgatca ctgggcctca gtggtgggct cgctgcaagc aaatgaacgt    5580
gctggactcc ttcatcaact actatgattc cgagaagcac gccgagaacg ccgtgatttt    5640
tctgcatggt aacgctacct ccagctacct gtggaggcac gtcgtgcctc acatcgagcc    5700
cgtggctaga tgcatcatcc ctgatctgat cggaatgggt aagtccggca agagcgggaa    5760
tggctcatat cgcctcctgg atcactacaa gtacctcacc gcttggttcg agctgctgaa    5820
ccttccaaag aaaatcatct ttgtgggcca cgactggggg agcgctctgg cctttcacta    5880
cgcctacgag caccaagaca ggatcaaggc catcgtccat atggagagtg tcgtggacgt    5940
gatcgagtcc tggatggggt ggcctgacat cgaggaggag ctggcccctga tcaagagcga    6000
agagggcgag aaaatggtgc ttgagaataa cttcttcgtc gagaccctgt tgccaagcaa    6060
gatcatgcgc aaactggagc ctgaggagtt cgctgcctac ctggagccat caaggagaa    6120
gggcgaggtt agacggccta ccctctcctg gcctcgcgag atccctctcg ttaagggagg    6180
caagcccgac gtcgtccaga ttgtccgcaa ctacaacgcc taccttcggg ccagcgacga    6240
tctgcctaag ctgttcatcg agtccgaccc tgggttctt tccaacgcta ttgtcgaggg    6300
agctaagaag ttccctaaca ccgagttcgt gaaggtgaag ggcctccact tcctccagga    6360
```

-continued

```
ggacgctcca gatgaaatgg gtaagtacat caagagcttc gtggagcgcg tgctgaagaa    6420
cgagcagtaa gaattcgata tcaagcttat cgataatcaa cctctggatt acaaaatttg    6480
tgaaagattg actggtattc ttaactatgt tgctccttt acgctatgtg gatacgctgc    6540
tttaatgcct ttgtatcatg ctattgcttc ccgtatggct ttcattttct cctccttgta    6600
taaatcctgg ttgctgtctc tttatgagga gttgtggccc gttgtcaggc aacgtggcgt    6660
ggtgtgcact gtgtttgctg acgcaacccc cactggttgg ggcattgcca ccacctgtca    6720
gctcctttcc gggactttcg ctttccccct ccctattgcc acggcggaac tcatcgccgc    6780
ctgccttgcc cgctgctgga caggggctcg gctgttgggc actgacaatt ccgtggtgtt    6840
gtcggggaaa tcatcgtcct tccttggct gctcgcctgt gttgccacct ggattctgcg    6900
cgggacgtcc ttctgctacg tcccttcggc cctcaatcca gcggaccttc cttcccgcgg    6960
cctgctgccg gctctgcggc ctcttccgcg tcttcgcctt cgccctcaga cgagtcggat    7020
ctccctttgg gccgcctccc cgcatcgata ccgtcgacct cgagacctag aaaaacatgg    7080
agcaatcaca gtagcaata cagcagctac caatgctgat tgtgcctggc tagaagcaca    7140
agaggaggag gaggtgggtt ttccagtcac acctcaggta cctttaagac caatgactta    7200
caaggcagct gtagatctta gccactttt aaaagaaaag gggggactgg aagggctaat    7260
tcactcccaa cgaagacaag atatccttga tctgtggatc taccacacac aaggctactt    7320
ccctgattgg cagaactaca caccagggcc agggatcaga tatccactga cctttggatg    7380
gtgctacaag ctagtaccag ttgagcaaga gaaggtagaa gaagccaatg aaggagagaa    7440
cacccgcttg ttacaccctg tgagcctgca tgggatggat gacccggaga gagaagtatt    7500
agagtggagg tttgacagcc gcctagcatt tcatcacatg gcccgagagc tgcatccgga    7560
ctgtactggg tctctctggt tagaccagat ctgagcctgg gagctctctg gctaactagg    7620
gaacccactg cttaagcctc aataaagctt gccttgagtg cttcaagtag tgtgtgcccg    7680
tctgttgtgt gactctggta actagagatc cctcagaccc ttttagtcag tgtggaaaat    7740
ctctagcagg gcccgtttaa acccgctgat cagcctcgac tgtgccttct agttgccagc    7800
catctgttgt ttgcccctcc cccgtgcctt ccttgaccct ggaaggtgcc actcccactg    7860
tcctttccta ataaaatgag gaaattgcat cgcattgtct gagtaggtgt cattctattc    7920
tggggggtgg ggtggggcag gacagcaagg gggaggattg ggaagacaat agcaggcatg    7980
ctggggatgc ggtgggctct atggcttctg aggcggaaag aaccagctgg ggctctaggg    8040
ggtatcccca cgcgccctgt agcggcgcat taagcgcggc gggtgtggtg gttacgcgca    8100
gcgtgaccgc tacacttgcc agcgccctag cgcccgctcc tttcgctttc ttcccttcct    8160
ttctcgccac gttcgccggc tttccccgtc aagctctaaa tcggggctc ctttagggt    8220 tccgatttag tgctttacgg cacctcgacc ccaaaaaact tgattagggt gatggttcac    8280
gtagtgggcc atcgccctga tagacggttt ttcgcccttt gacgttggag tccacgttct    8340
ttaatagtgg actcttgttc caaactggaa caacactcaa ccctatctcg gtctattctt    8400
ttgatttata agggattttg ccgatttcgg cctattggtt aaaaaatgag ctgatttaac    8460
aaaaatttaa cgcgaattaa ttctgtggaa tgtgtgtcag ttgggtgtg aaagtcccc    8520 aggctcccca gcaggcagaa gtatgcaaag catgcatctc aattagtcag caaccaggtg    8580
tggaaagtcc ccaggctccc cagcaggcag aagtatgcaa agcatgcatc tcaattagtc    8640
agcaaccata gtcccgcccc taactccgcc catcccgccc taactccgcc ccagttccgc    8700
```

```
ccattctccg ccccatggct gactaatttt ttttatttat gcagaggccg aggccgcctc    8760
tgcctctgag ctattccaga agtagtgagg aggcttttt ggaggcctag gcttttgcaa     8820
aaagctcccg ggagcttgta tatccatttt cggatctgat cagcacgtgt tgacaattaa    8880
tcatcggcat agtatatcgg catagtataa tacgacaagg tgaggaacta aaccatggcc    8940
aagttgacca gtgccgttcc ggtgctcacc gcgcgcgacg tcgccggagc ggtcgagttc    9000
tggaccgacc ggctcgggtt ctcccgggac ttcgtggagg acgacttcgc cggtgtggtc    9060
cgggacgacg tgaccctgtt catcagcgcg gtccaggacc aggtggtgcc ggacaacacc    9120
ctggcctggg tgtgggtgcg cggcctggac gagctgtacg ccgagtggtc ggaggtcgtg    9180
tccacgaact tccgggacgc ctccgggccg gccatgaccg agatcggcga gcagccgtgg    9240
gggcgggagt tcgccctgcg cgacccggcc ggcaactgcg tgcacttcgt ggccgaggag    9300
caggactgac acgtgctacg agatttcgat tccaccgccg ccttctatga aaggttgggc    9360
ttcggaatcg ttttccggga cgccggctgg atgatcctcc agcgcgggga tctcatgctg    9420
gagttcttcg cccaccccaa cttgtttatt gcagcttata atggttacaa ataaagcaat    9480
agcatcacaa atttcacaaa taaagcattt ttttcactgc attctagttg tggtttgtcc    9540
aaactcatca atgtatctta tcatgtctgt ataccgtcga cctctagcta gagcttggcg    9600
taatcatggt catagctgtt tcctgtgtga aattgttatc cgctcacaat tccacacaac    9660
atacgagccg gaagcataaa gtgtaaagcc tggggtgcct aatgagtgag ctaactcaca    9720
ttaattgcgt tgcgctcact gcccgctttc cagtcgggaa acctgtcgtg ccagctgcat    9780
taatgaatcg gccaacgcgc ggggagaggc ggtttgcgta ttgggcgctc ttccgcttcc    9840
tcgctcactg actcgctgcg ctcggtcgtt cggctgcggc gagcggtatc agctcactca    9900
aaggcggtaa tacggttatc cacagaatca ggggataacg caggaaagaa catgtgagca    9960
aaaggccagc aaaaggccag gaaccgtaaa aaggccgcgt tgctggcgtt tttccatagg   10020
ctccgccccc ctgacgagca tcacaaaaat cgacgctcaa gtcagaggtg gcgaaacccg   10080
acaggactat aaagatacca ggcgtttccc cctggaagct ccctcgtgcg ctctcctgtt   10140
ccgaccctgc cgcttaccgg atacctgtcc gcctttctcc cttcgggaag cgtggcgctt   10200
tctcatagct cacgctgtag gtatctcagt tcggtgtagg tcgttcgctc caagctgggc   10260
tgtgtgcacg aaccccccgt tcagcccgac cgctgcgcct tatccggtaa ctatcgtctt   10320
gagtccaacc cggtaagaca cgacttatcg ccactggcag cagccactgg taacaggatt   10380
agcagagcga ggtatgtagg cggtgctaca gagttcttga agtggtggcc taactacggc   10440
tacactagaa gaacagtatt tggtatctgc gctctgctga agccagttac cttcggaaaa   10500
agagttggta gctcttgatc cggcaaacaa accaccgctg gtagcggtgg ttttttttgtt   10560
tgcaagcagc agattacgcg cagaaaaaaa ggatctcaag aagatccttt gatcttttct   10620
acggggtctg acgctcagtg gaacgaaaac tcacgttaag ggattttggt catgagatta   10680
tcaaaaagga tcttcaccta gatcctttta aattaaaaat gaagttttaa atcaatctaa   10740
agtatatatg agtaaacttg gtctgacagt taccaatgct taatcagtga ggcacctatc   10800
tcagcgatct gtctatttcg ttcatccata gttgcctgac tccccgtcgt gtagataact   10860
acgatacggg agggcttacc atctggcccc agtgctgcaa tgataccgcg agacccacgc   10920
tcaccggctc cagatttatc agcaataaac cagccagccg aagggccga gcgcagaagt   10980
ggtcctgcaa ctttatccgc ctccatccag tctattaatt gttgccggga agctagagta   11040
agtagttcgc cagttaatag tttgcgcaac gttgttgcca ttgctacagg catcgtggtg   11100
```

```
tcacgctcgt cgtttggtat ggcttcattc agctccggtt cccaacgatc aaggcgagtt    11160
acatgatccc ccatgttgtg caaaaaagcg gttagctcct tcggtcctcc gatcgttgtc    11220
agaagtaagt tggccgcagt gttatcactc atggttatgg cagcactgca taattctctt    11280
actgtcatgc catccgtaag atgctttttct gtgactggtg agtactcaac caagtcattc   11340
tgagaatagt gtatgcggcg accgagttgc tcttgcccgg cgtcaatacg ggataatacc    11400
gcgccacata gcagaacttt aaaagtgctc atcattggaa aacgttcttc ggggcgaaaa    11460
ctctcaagga tcttaccgct gttgagatcc agttcgatgt aacccactcg tgcacccaac    11520
tgatcttcag catcttttac tttcaccagc gtttctgggt gagcaaaaac aggaaggcaa    11580
aatgccgcaa aaagggaat aagggcgaca cggaaatgtt gaatactcat actcttcctt     11640
tttcaatatt attgaagcat ttatcagggt tattgtctca tgagcggata catatttgaa    11700
tgtatttaga aaataaaca aatagggggtt ccgcgcacat ttccccgaaa agtgccacct    11760
gac                                                                  11763
```

<210> SEQ ID NO 5
<211> LENGTH: 290
<212> TYPE: PRT
<213> ORGANISM: Artificial
<220> FEATURE:
<223> OTHER INFORMATION: Synthetic construct

<400> SEQUENCE: 5

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240
```

```
Val Gly Val Thr Ser Trp Gly Tyr Ser Phe Leu Asp Ile Val Ala Lys
            245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
            275                 280                 285

Ala Asp
    290

<210> SEQ ID NO 6
<211> LENGTH: 291
<212> TYPE: PRT
<213> ORGANISM: Artificial
<220> FEATURE:
<223> OTHER INFORMATION: Synthetic construct

<400> SEQUENCE: 6

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
            245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
            275                 280                 285

Ala Asp Asp
    290
```

<210> SEQ ID NO 7
<211> LENGTH: 248
<212> TYPE: PRT
<213> ORGANISM: Artificial
<220> FEATURE:
<223> OTHER INFORMATION: Synthetic construct

<400> SEQUENCE: 7

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Met Leu Ile
            20                  25                  30

Gly Thr Phe Tyr Phe Ile Val Lys Gly Trp Gly Val Thr Asp Lys Glu
            35                  40                  45

Ala Arg Glu Tyr Tyr Ser Ile Thr Ile Leu Val Pro Gly Ile Ala Ser
        50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
        115                 120                 125

Ile Val Thr Gly Leu Ile Gly Ala Leu Ser His Thr Pro Leu Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245

<210> SEQ ID NO 8
<211> LENGTH: 311
<212> TYPE: PRT
<213> ORGANISM: Artificial
<220> FEATURE:
<223> OTHER INFORMATION: Synthetic construct

<400> SEQUENCE: 8

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val

```
Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 9
<211> LENGTH: 238
<212> TYPE: PRT
<213> ORGANISM: Artificial
<220> FEATURE:
<223> OTHER INFORMATION: Synthetic construct

<400> SEQUENCE: 9

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Gly Tyr Gly Leu Gln Cys Phe Ala Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
```

|   |   |   |   |   |   |   |   |   |   |
|---|---|---|---|---|---|---|---|---|---|
|   |   | 100 |   |   | 105 |   |   | 110 |   |

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
            195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 10
<211> LENGTH: 239
<212> TYPE: PRT
<213> ORGANISM: Artificial
<220> FEATURE:
<223> OTHER INFORMATION: Synthetic construct

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys

<210> SEQ ID NO 11
<211> LENGTH: 839
<212> TYPE: PRT
<213> ORGANISM: Artificial
<220> FEATURE:
<223> OTHER INFORMATION: Synthetic construct

<400> SEQUENCE: 11

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp Ala Ala Val Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Gln Cys Phe Ala Arg Tyr

-continued

```
            355                 360                 365
Pro Asp His Met Lys Gln His Asp Phe Phe Lys Ser Ala Met Pro Glu
370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Asp Phe Lys Glu Asp Gly Asn Ile Leu Gly
                420                 425                 430

His Lys Leu Glu Tyr Asn Tyr Asn Ser His Asn Val Tyr Ile Thr Ala
            435                 440                 445

Asp Lys Gln Lys Asn Gly Ile Lys Ala Asn Phe Lys Ile Arg His Asn
450                 455                 460

Ile Glu Asp Gly Gly Val Gln Leu Ala Asp His Tyr Gln Gln Asn Thr
465                 470                 475                 480

Pro Ile Gly Asp Gly Pro Val Leu Leu Pro Asp Asn His Tyr Leu Ser
                485                 490                 495

Tyr Gln Ser Lys Leu Ser Lys Asp Pro Asn Glu Lys Arg Asp His Met
                500                 505                 510

Val Leu Leu Glu Phe Val Thr Ala Ala Gly Gly Thr Lys Val Tyr Asp
            515                 520                 525

Pro Glu Gln Arg Lys Arg Met Ile Thr Gly Pro Gln Trp Trp Ala Arg
530                 535                 540

Cys Lys Gln Met Asn Val Leu Asp Ser Phe Ile Asn Tyr Tyr Asp Ser
545                 550                 555                 560

Glu Lys His Ala Glu Asn Ala Val Ile Phe Leu His Gly Asn Ala Thr
                565                 570                 575

Ser Ser Tyr Leu Trp Arg His Val Val Pro His Ile Glu Pro Val Ala
            580                 585                 590

Arg Cys Ile Ile Pro Asp Leu Ile Gly Met Gly Lys Ser Gly Lys Ser
            595                 600                 605

Gly Asn Gly Ser Tyr Arg Leu Leu Asp His Tyr Lys Tyr Leu Thr Ala
610                 615                 620

Trp Phe Glu Leu Leu Asn Leu Pro Lys Lys Ile Ile Phe Val Gly His
625                 630                 635                 640

Asp Trp Gly Ala Ala Leu Ala Phe His Tyr Ala Tyr Glu His Gln Asp
                645                 650                 655

Arg Ile Lys Ala Ile Val His Met Glu Ser Val Val Asp Val Ile Glu
                660                 665                 670

Ser Trp Asp Glu Trp Pro Asp Ile Glu Glu Asp Ile Ala Leu Ile Lys
            675                 680                 685

Ser Glu Glu Gly Glu Lys Met Val Leu Glu Asn Asn Phe Phe Val Glu
            690                 695                 700

Thr Val Leu Pro Ser Lys Ile Met Arg Lys Leu Glu Pro Glu Glu Phe
705                 710                 715                 720

Ala Ala Tyr Leu Glu Pro Phe Lys Glu Lys Gly Glu Val Arg Arg Pro
                725                 730                 735

Thr Leu Ser Trp Pro Arg Glu Ile Pro Leu Val Lys Gly Gly Lys Pro
                740                 745                 750

Asp Val Val Gln Ile Val Arg Asn Tyr Asn Ala Tyr Leu Arg Ala Ser
            755                 760                 765

Asp Asp Leu Pro Lys Leu Phe Ile Glu Gly Asp Pro Gly Phe Phe Ser
770                 775                 780
```

```
Asn Ala Ile Val Glu Gly Ala Lys Lys Phe Pro Asn Thr Glu Phe Val
785                 790                 795                 800

Lys Val Lys Gly Leu His Phe Leu Gln Glu Asp Ala Pro Asp Glu Met
            805                 810                 815

Gly Lys Tyr Ile Lys Ser Phe Val Glu Arg Val Leu Asn Glu Gln
        820                 825                 830

Phe Cys Tyr Glu Asn Glu Val
        835

<210> SEQ ID NO 12
<211> LENGTH: 12249
<212> TYPE: DNA
<213> ORGANISM: Artificial
<220> FEATURE:
<223> OTHER INFORMATION: Synthetic construct

<400> SEQUENCE: 12
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
```

-continued

```
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggggat    2460 tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtggggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt gggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420 accttttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
gataagtgag gcgtcagttt cttggtcgg tttatgtac ctatcttctt aagtagctga    3660
agctccggtt ttgaactatg cgctcggggt tggcgagtgt gttttgtgaa gttttttagg    3720 cacctttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tccatgacag agaccctgcc tcccgtgacc gagagtgccg tggcccttca    3900
agccgaggtt acccaaaggg agttgttcga gttcgtgctg aacgacccct tgcttgcaag    3960
cagtctctat atcaacatcg cacttgcagg actgagtata ctgctgttcg ttttttatgac    4020 ccgaggactc gatgatccac gggcaaaact tattgctgtg tcaaccatcc ttgtgcctgt    4080
```

```
cgtcagcatt gcctcctaca ctggattggc gagcggcctg acaatttccg ttcttgaaat    4140
gccagcgggc cattttgcag aaggcagctc agtgatgctg ggaggagaag aggtagatgg    4200
tgtagtcacc atgtggggac ggtatctcac ctgggcactt ccacgccca tgattctcct    4260
cgctctgggt ctcctggccg aagcaatgc tacaaagctc ttcacagcta tcactttcga    4320
tatcgctatg tgcgtgactg gccttgccgc ggccctgact acctcctccc acctcatgag    4380
atggttctgg tacgctatca gttgtgcatg ctttctggtg gtcttgtata tcctgctggt    4440
ggagtgggca caggacgcca aagccgcggg aaccgctgac atgttcaata ccctgaagct    4500
gttgacagta gtgatgtggc tggggtatcc aattgtgtgg gctcttggag tcagggtat    4560
cgcggtgttg cccgttgggg tgacgagctg gggatattct ttcctggata tcgtggcaaa    4620
gtacattttc gcattcttgc tcctgaacta tctgacgtca aacgaatctg tcgtgtccgg    4680
cagcattttg gatgttccat ctgcttctgg accccggct gatgatgcgg ccgcagtgag    4740
caagggcgag gagctgttca ccggggtggt gcccatcctg gtcgagctgg acggcgacgt    4800
aaacggccac aagttcagcg tgtccggcga gggcgagggc gatgccacct acggcaagct    4860
gacccctgaag ctgatctgca ccaccggcaa gctgcccgtg ccctggccca ccctcgtgac    4920
caccctgggc tacggcctgc agtgcttcgc ccgctacccc gaccacatga gcagcacga    4980
cttcttcaag tccgccatgc ccgaaggcta cgtccaggag cgcaccatct tcttcaagga    5040
cgacggcaac tacaagaccc gcgccgaggt gaagttcgag ggcgacaccc tggtgaaccg    5100
catcgagctg aagggcatcg acttcaagga ggacggcaac atcctggggc acaagctgga    5160
gtacaactac aacagccaca cgtctatat caccgccgac aagcagaaga cggcatcaa    5220
ggccaacttc aagatccgcc acaacatcga ggacggcggc gtgcagctcg ccgaccacta    5280
ccagcagaac ccccccatcg gcgacggccc cgtgctgctg cccgacaacc actacctgag    5340
ctaccagtcc aagctgagca agaccccaa cgagaagcgc gatcacatgg tcctgctgga    5400
gttcgtgacc gccgccgggg gtaccaaggt gtacgacccc gagcagagga agaggatgat    5460
caccggcccc cagtggtggg ccaggtgcaa gcagatgaac gtgctggaca gcttcatcaa    5520
ctactacgac agcgagaagc acgccgagaa cgccgtgatc ttcctgcacg caacgccac    5580
tagcagctac ctgtggaggc acgtggtgcc ccacatcgag cccgtggcca ggtgcatcat    5640
ccccgatctg atcggcatgg gcaagagcgg caagagcggc aacggcagct acaggctgct    5700
ggaccactac aagtacctga ccgcctggtt cgagctcctg aacctgccca agaagatcat    5760
cttcgtgggc cacgactggg gcgccgccct ggccttccac tacgcctacg agcaccagga    5820
caggatcaag gccatcgtgc acatggagag cgtggtggac gtgatcgaga gctgggacga    5880
gtggccagac atcgaggagg acatcgccct gatcaagagc gaggagggcg agaagatggt    5940
gctggagaac aacttcttcg tggagaccgt gctgcccagc aagatcatga aaagctgga    6000
gcccgaggag ttcgccgcct acctggagcc cttcaaggag aagggcgagg tgaagaagacc    6060
caccctgagc tggcccagag agatccccct ggtgaagggc ccatggatgc atgaccaact    6120
gacagaagag cagattgcag agttcaaaga agccttctca ttattcgaca aggatgggga    6180
cggcaccatc accacaaagg aacttggcac cgttatgagg tcgcttggac aaacccaac    6240
ggaagcagaa ttgcaggata tgatcaatga agtcgatgct gatggcaatg aacgatttta    6300
ctttcctgaa tttcttacta tgatggctag aaaaatgaag gacacagaca gcgaagagga    6360
aatccgagaa gcattccgtg tttttgacaa ggatgggaac ggctacatca gcgctgctca    6420
```

```
gttacgtcac gtcatgacaa acctcgggga gaagttaaca gatgaagaag ttgatgaaat    6480
gataagggaa gcagatatcg atggtgatgg ccaagtaaac tatgaagagt ttgtacaaat    6540
gatgacagca aagggggga agaggcgctg aagaaaaac ttcattgccg tcagcgctgc      6600
caaccggttc aagaagatct ccagctccgg ggcactggag ctcggcaagc ccgacgtggt    6660
gcagatcgtg agaaactaca acgcctacct gagagccagc gacgacctgc ccaagctgtt    6720
catcgagggc gacccggct tcttcagcaa cgccatcgtg gagggcgcca agaagttccc      6780
caacaccgag ttcgtgaagg tgaagggcct gcacttcctc caggaggacg cccccgacga    6840
gatgggcaag tacatcaaga gcttcgtgga gagagtgctg aagaacgagc agttctgcta    6900
cgagaacgag gtgtaagaat tcgatatcaa gcttatcgat aatcaacctc tggattacaa    6960
aatttgtgaa agattgactg gtattcttaa ctatgttgct ccttttacgc tatgtggata    7020
cgctgcttta atgcctttgt atcatgctat tgcttcccgt atggctttca ttttctcctc    7080
cttgtataaa tcctggttgc tgtctcttta tgaggagttg tggcccgttg tcaggcaacg    7140
tggcgtggtg tgcactgtgt tgctgacgc aaccccact ggttgggca ttgccaccac       7200 ctgtcagctc ctttccggga ctttcgcttt cccctcct attgccacgg cggaactcat      7260
cgccgcctgc cttgcccgct gctggacagg ggctcggctg ttgggcactg acaattccgt    7320
ggtgttgtcg gggaaatcat cgtccttttcc ttggctgctc gcctgtgttg ccacctggat   7380 tctgcgcgg acgtccttct gctacgtccc ttcggccctc aatccagcgg accttccttc     7440
ccgcggcctg ctgccggctc tgcggcctct tccgcgtctt cgccttcgcc ctcagacgag    7500
tcggatctcc ctttgggccg cctccccgca tcgataccgt cgacctcgag acctagaaaa    7560
acatggagca atcacaagta gcaatacagc agctaccaat gctgattgtg cctggctaga    7620
agcacaagag gaggaggagg tgggttttcc agtcacacct caggtacctt taagaccaat    7680
gacttacaag gcagctgtag atcttagcca ctttttaaaa gaaaaggggg gactggaagg    7740
gctaattcac tcccaacgaa gacaagatat ccttgatctg tggatctacc acacacaagg    7800
ctacttccct gattggcaga actacacacc agggccaggg atcagatatc cactgacctt    7860
tggatggtgc tacaagctag taccagttga gcaagagaag gtagaagaag ccaatgaagg    7920
agagaacacc cgcttgttac accctgtgag cctgcatggg atggatgacc cggagagaga    7980
agtattagag tggaggtttg acagccgcct agcatttcat cacatggccc gagagctgca    8040
tccggactgt actgggtctc tctggttaga ccagatctga gcctgggagc tctctggcta    8100
actagggaac ccactgctta agcctcaata aagcttgcct tgagtgcttc aagtagtgtg    8160
tgcccgtctg ttgtgtgact ctggtaacta gagatccctc agacccttt agtcagtgtg    8220 gaaaatctct agcagggccc gtttaaaccc gctgatcagc ctcgactgtg ccttctagtt    8280
gccagccatc tgttgtttgc ccctccccg tgccttcctt gaccctggaa ggtgccactc     8340
ccactgtcct ttcctaataa aatgaggaaa ttgcatcgca ttgtctgagt aggtgtcatt    8400
ctattctggg gggtggggtg gggcaggaca gcaaggggga ggattgggaa gacaatagca    8460
ggcatgctgg ggatgcggtg ggctctatgg cttctgaggc ggaaagaacc agctggggct    8520
ctagggggta tccccacgcg ccctgtagcg gcgcattaag cgcggcgggt gtggtggtta    8580
cgcgcagcgt gaccgctaca cttgccagcg ccctagcgcc cgctcctttc gctttcttcc    8640
cttcctttct cgccacgttc gccggctttc cccgtcaagc tctaaatcgg ggctccctt     8700 tagggttccg atttagtgct ttacggcacc tcgaccccaa aaaacttgat tagggtgatg    8760
gttcacgtag tgggccatcg ccctgataga cggtttttcg ccctttgacg ttggagtcca    8820
```

-continued

```
cgttctttaa tagtggactc ttgttccaaa ctggaacaac actcaaccct atctcggtct   8880
attcttttga tttataaggg attttgccga tttcggccta ttggttaaaa aatgagctga   8940
tttaacaaaa atttaacgcg aattaattct gtggaatgtg tgtcagttag ggtgtggaaa   9000
gtccccaggc tccccagcag gcagaagtat gcaaagcatg catctcaatt agtcagcaac   9060
caggtgtgga aagtccccag gctccccagc aggcagaagt atgcaaagca tgcatctcaa   9120
ttagtcagca accatagtcc cgcccctaac tccgcccatc ccgcccctaa ctccgcccag   9180
ttccgcccat tctccgcccc atggctgact aatttttttt atttatgcag aggccgaggc   9240
cgcctctgcc tctgagctat tccagaagta gtgaggaggc ttttttggag gcctaggctt   9300
ttgcaaaaag ctcccgggag cttgtatatc cattttcgga tctgatcagc acgtgttgac   9360
aattaatcat cggcatagta tatcggcata gtataatacg acaaggtgag gaactaaacc   9420
atggccaagt tgaccagtgc cgttccggtg ctcaccgcgc gcgacgtcgc cggagcggtc   9480
gagttctgga ccgaccggct cgggttctcc cggacttcg tggaggacga cttcgccggt   9540
gtggtccggg acgacgtgac cctgttcatc agcgcggtcc aggaccaggt ggtgccggac   9600
aacaccctgg cctgggtgtg ggtgcgcggc ctggacgagc tgtacgccga gtggtcggag   9660
gtcgtgtcca cgaacttccg ggacgcctcc gggccggcca tgaccgagat cggcgagcag   9720
ccgtggggc gggagttcgc cctgcgcgac cggccggca actgcgtgca cttcgtggcc   9780
gaggagcagg actgacacgt gctacgagat ttcgattcca ccgccgcctt ctatgaaagg   9840
ttgggcttcg gaatcgtttt ccgggacgcc ggctggatga tcctccagcg cggggatctc   9900
atgctggagt tcttcgccca ccccaacttg tttattgcag cttataatgg ttacaaataa   9960
agcaatagca tcacaaattt cacaaataaa gcattttttt cactgcattc tagttgtggt  10020
ttgtccaaac tcatcaatgt atcttatcat gtctgtatac cgtcgacctc tagctagagc  10080
ttggcgtaat catggtcata gctgtttcct gtgtgaaatt gttatccgct cacaattcca  10140
cacaacatac gagccggaag cataaagtgt aaagcctggg gtgcctaatg agtgagctaa  10200
ctcacattaa ttgcgttgcg ctcactgccc gctttccagt cgggaaacct gtcgtgccag  10260
ctgcattaat gaatcggcca acgcgcgggg agaggcggtt tgcgtattgg gcgctcttcc  10320
gcttcctcgc tcactgactc gctgcgctcg tcgttcggc tgcggcgagc ggtatcagct  10380
cactcaaagg cggtaatacg gttatccaca gaatcagggg ataacgcagg aaagaacatg  10440
tgagcaaaag gccagcaaaa ggccaggaac cgtaaaaagg ccgcgttgct ggcgtttttc  10500
cataggctcc gcccccctga cgagcatcac aaaaatcgac gctcaagtca gaggtggcga  10560
aacccgacag gactataaag ataccaggcg tttccccctg gaagctccct cgtgcgctct  10620
cctgttccga ccctgccgct taccggatac ctgtccgcct ttctcccttc gggaagcgtg  10680
gcgctttctc atagctcacg ctgtaggtat ctcagttcgg tgtaggtcgt tcgctccaag  10740
ctgggctgtg tgcacgaacc ccccgttcag cccgaccgct gcgccttatc cggtaactat  10800
cgtcttgagt ccaacccggt aagacacgac ttatcgccac tggcagcagc cactggtaac  10860
aggattagca gagcgaggta tgtaggcggt gctacagagt tcttgaagtg gtggcctaac  10920
tacggctaca ctagaagaac agtatttggt atctgcgctc tgctgaagcc agttaccttc  10980
ggaaaaagag ttggtagctc ttgatccggc aaacaaacca ccgctggtag cggtggtttt  11040
tttgtttgca agcagcagat tacgcgcaga aaaaaaggat ctcaagaaga tcctttgatc  11100
ttttctacgg ggtctgacgc tcagtggaac gaaaactcac gttaagggat tttggtcatg  11160
```

| | | | | |
|---|---|---|---|---|
| agattatcaa | aaaggatctt | cacctagatc | cttttaaatt | aaaaatgaag ttttaaatca | 11220 |
| atctaaagta | tatatgagta | aacttggtct | gacagttacc | aatgcttaat cagtgaggca | 11280 |
| cctatctcag | cgatctgtct | atttcgttca | tccatagttg | cctgactccc cgtcgtgtag | 11340 |
| ataactacga | tacgggaggg | cttaccatct | ggccccagtg | ctgcaatgat accgcgagac | 11400 |
| ccacgctcac | cggctccaga | tttatcagca | ataaaccagc | cagccggaag ggccgagcgc | 11460 |
| agaagtggtc | ctgcaacttt | atccgcctcc | atccagtcta | ttaattgttg ccgggaagct | 11520 |
| agagtaagta | gttcgccagt | taatagtttg | cgcaacgttg | ttgccattgc tacaggcatc | 11580 |
| gtggtgtcac | gctcgtcgtt | tggtatggct | tcattcagct | ccggttccca acgatcaagg | 11640 |
| cgagttacat | gatccccat | gttgtgcaaa | aaagcggtta | gctccttcgg tcctccgatc | 11700 |
| gttgtcagaa | gtaagttggc | cgcagtgtta | tcactcatgg | ttatggcagc actgcataat | 11760 |
| tctcttactg | tcatgccatc | cgtaagatgc | ttttctgtga | ctggtgagta ctcaaccaag | 11820 |
| tcattctgag | aatagtgtat | gcggcgaccg | agttgctctt | gcccggcgtc aatacgggat | 11880 |
| aataccgcgc | cacatagcag | aactttaaaa | gtgctcatca | ttggaaaacg ttcttcgggg | 11940 |
| cgaaaactct | caaggatctt | accgctgttg | agatccagtt | cgatgtaacc cactcgtgca | 12000 |
| cccaactgat | cttcagcatc | ttttactttc | accagcgttt | ctgggtgagc aaaaacagga | 12060 |
| aggcaaaatg | ccgcaaaaaa | gggaataagg | gcgacacgga | aatgttgaat actcatactc | 12120 |
| ttcctttttc | aatattattg | aagcatttat | cagggttatt | gtctcatgag cggatacata | 12180 |
| tttgaatgta | tttagaaaaa | taaacaaata | ggggttccgc | gcacatttcc ccgaaaagtg | 12240 |
| ccacctgac | | | | | 12249 |

<210> SEQ ID NO 13
<211> LENGTH: 11706
<212> TYPE: DNA
<213> ORGANISM: Artificial
<220> FEATURE:
<223> OTHER INFORMATION: Synthetic construct

<400> SEQUENCE: 13

| | | | | |
|---|---|---|---|---|
| gtcgacggat | cgggagatct | cccgatcccc | tatggtgcac | tctcagtaca atctgctctg | 60 |
| atgccgcata | gttaagccag | tatctgctcc | ctgcttgtgt | gttggaggtc gctgagtagt | 120 |
| gcgcgagcaa | aatttaagct | acaacaaggc | aaggcttgac | cgacaattgc atgaagaatc | 180 |
| tgcttagggt | taggcgtttt | cgcgctgctt | cgcgatgtacg | ggccagatat acgcgttgac | 240 |
| attgattatt | gactagttat | taatagtaat | caattacggg | gtcattagtt catagcccat | 300 |
| atatggagtt | ccgcgttaca | taacttacgg | taaatggccc | gcctggctga ccgcccaacg | 360 |
| acccccgccc | attgacgtca | ataatgacgt | atgttcccat | agtaacgcca atagggactt | 420 |
| tccattgacg | tcaatgggtg | gagtatttac | ggtaaactgc | ccacttggca gtacatcaag | 480 |
| tgtatcatat | gccaagtacg | cccctattg | acgtcaatga | cggtaaatgg cccgcctggc | 540 |
| attatgccca | gtacatgacc | ttatgggact | ttcctacttg | gcagtacatc tacgtattag | 600 |
| tcatcgctat | taccatggtg | atgcggtttt | ggcagtacat | caatgggcgt ggatagcggt | 660 |
| ttgactcacg | gggatttcca | agtctccacc | ccattgacgt | caatgggagt ttgttttggc | 720 |
| accaaaatca | acgggacttt | ccaaaatgtc | gtaacaactc | cgccccattg acgcaaatgg | 780 |
| gcggtaggcg | tgtacggtgg | gaggtctata | taagcagcgc | gttttgcctg tactgggtct | 840 |
| ctctggttag | accagatctg | agcctgggag | ctctctggct | aactagggaa cccactgctt | 900 |
| aagcctcaat | aaagcttgcc | ttgagtgctt | caagtagtgt | gtgcccgtct gttgtgtgac | 960 |

```
tctggtaact agagatccct cagacccttt tagtcagtgt ggaaaatctc tagcagtggc    1020
gcccgaacag ggacttgaaa gcgaaaggga aaccagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctgggaatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggat    2460 tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtgggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggcggggct ttcgtggccg ccgggccgct    3060
cggtgggacg gaagcgtgtg gagagaccgc caagggctgt agtctgggtc cgcgagcaag    3120
gttgccctga actgggggtt ggggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
```

-continued

```
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgagggagg     3600 gataagtgag gcgtcagttt cttggtcgg ttttatgtac ctatcttctt aagtagctga     3660
agctccggtt ttgaactatg cgctcggggt tggcgagtgt gttttgtgaa gtttttagg     3720 cacctttga aatgtaatca tttgggtcaa tatgtaattt tcagtgttag actagtaaag     3780
cttctgcagg tcgactctag aaaattgtcc gctaaattct ggccgttttt ggctttttg     3840 ttagacagga tccatgacag agaccctgcc tcccgtgacc gagagtgccg tggcccttca    3900
agccgaggtt acccaagggg agttgttcga gttcgtgctg aacgaccctt tgcttgcaag    3960
cagtctctat atcaacatcg cacttgcagg actgagtata ctgctgttcg tttttatgac    4020
ccgaggactc gatgatccac gggcaaaact tattgctgtg tcaaccatcc ttgtgcctgt    4080
cgtcagcatt gcctcctaca ctggattggc gagcggcctg acaatttccg ttcttgaaat    4140
gccagcgggc cattttgcag aaggcagctc agtgatgctg ggaggagaag aggtagatgg    4200
tgtagtcacc atgtggggac ggtatctcac ctgggcactt tccacgccca tgattctcct    4260
cgctctgggt ctcctggccg gaagcaatgc tacaaagctc ttcacagcta tcactttcga    4320
tatcgctatg tgcgtgactg gccttgccgc ggccctgact acctcctccc acctcatgag    4380
atggttctgg tacgctatca gttgtgcatg ctttctggtg gtcttgtata tcctgctggt    4440
ggagtgggca caggacgcca aagccgcggg aaccgctgac atgttcaata ccctgaagct    4500
gttgacagta tgtgatgtggc tggggtatcc aattgtgtgg gctcttggag tcgagggtat    4560
cgcggtgttg cccgttgggg tgacgagctg gggatattct ttcctggata tcgtggcaaa    4620 gtacatttc gcattcttgc tcctgaacta tctgacgtca aacgaatctg tcgtgtccgg    4680
cagcattttg gatgttccat ctgcttctgg daccccggct gatgatgcgg ccgcagtgag    4740
caagggcgag gagctgttca ccggggtggt gcccatcctg gtcgagctgg acggcgacgt    4800
aaacggccac aagttcagcg tgtccggcga gggcgagggc gatgccacct acggcaagct    4860
gaccctgaag ctgatctgca ccaccggcaa gctgcccgtg ccctggccca ccctcgtgac    4920
cacccctggg tacggcctgc agtgcttcgc ccgctacccc gaccacatga agcagcacga    4980
cttcttcaag tccgccatgc ccgaaggcta cgtccaggag cgcaccatct tcttcaagga    5040
cgacggcaac tacaagaccc gcgccgaggt gaagttcgag ggcgacaccc tggtgaaccg    5100
catcgagctg aagggcatcg acttcaagga ggacggcaac atcctggggc acaagctgga    5160
gtacaactac aacagccaca cgtctatat caccgccgac aagcagaaga acggcatcaa    5220
ggccaacttc aagatccgcc acaacatcga ggacggcggc gtgcagctcg ccgaccacta    5280
ccagcagaac acccccatcg gcgacggccc cgtgctgctg cccgacaacc actacctgag    5340
ctaccagtcc aagctgagca agacccccaa cgagaagcgc gatcacatgg tcctgctgga    5400
gttcgtgacc gccgccgggg gtaccaaggt gtacgacccc gagcagagga agaggatgat    5460
caccggcccc cagtggtggg ccaggtgcaa gcagatgaac gtgctggaca gcttcatcaa    5520
ctactacgac agcgagaagc acgccgagaa cgccgtgatc ttcctgcacg gcaacgccac    5580
tagcagctac ctgtgagggc acgtggtgcc ccacatcgag cccgtggcca ggtgcatcat    5640
ccccgatctg atcggcatgg gcaagagcgg caagagcggc aacggcagct acaggctgct    5700
```

```
ggaccactac aagtacctga ccgcctggtt cgagcttctg aacctgccca agaagatcat    5760
cttcgtgggc cacgactggg cgccgccct ggccttccac tacgcctacg agcaccagga    5820
caggatcaag gccatcgtgc acatggagag cgtggtggac gtgatcgaga gctgggacga    5880
gtggccagac atcgaggagg acatcgccct gatcaagagc gaggagggcg agaagatggt    5940
gctggagaac aacttcttcg tggagaccgt gctgcccagc aagatcatga aaagctgga    6000 gcccgaggag ttcgccgcct acctggagcc cttcaaggag aagggcgagg tgagaagacc    6060
caccctgagc tggcccagag agatcccct ggtgaagggc ggcaagcccg acgtggtgca    6120
gatcgtgaga aactacaacg cctacctgag agccagcgac gacctgccca agctgttcat    6180
cgagggcgac cccggcttct tcagcaacgc catcgtggag ggcgccaaga agttccccaa    6240
caccgagttc gtgaaggtga agggcctgca cttcctccag gaggacgccc ccgacgagat    6300
gggcaagtac atcaagagct cgtggagag agtgctgaag aacgagcagt tctgctacga    6360
gaacgaggtg taagaattcg atatcaagct tatcgataat caacctctgg attacaaaat    6420
ttgtgaaaga ttgactggta ttcttaacta tgttgctcct tttacgctat gtggatacgc    6480
tgctttaatg ccttttgtatc atgctattgc ttcccgtatg gctttcattt tctcctcctt    6540
gtataaatcc tggttgctgt ctctttatga ggagttgtgg cccgttgtca ggcaacgtgg    6600
cgtggtgtgc actgtgtttg ctgacgcaac ccccactggt tggggcattg ccaccacctg    6660
tcagctcctt tccgggactt tcgctttccc cctccctatt gccacggcgg aactcatcgc    6720
cgcctgcctt gcccgctgct ggacagggc tcggctgttg ggcactgaca attccgtggt    6780
gttgtcgggg aaatcatcgt cctttccttg gctgctcgcc tgtgttgcca cctggattct    6840
gcgcgggacg tccttctgct acgtcccttc ggccctcaat ccagcggacc ttccttcccg    6900
cggcctgctg ccggctctgc ggcctcttcc gcgtcttcgc cttcgccctc agacgagtcg    6960
gatctccctt tgggccgcct ccccgcatcg ataccgtcga cctcgagacc tagaaaaaca    7020
tggagcaatc acaagtagca atacagcagc taccaatgct gattgtgcct ggctagaagc    7080
acaagaggag gaggagtgg gttttccagt cacacctcag gtacctttaa gaccaatgac    7140
ttacaaggca gctgtagatc ttagccactt ttttaaaagaa aagggggac tggaagggct    7200 aattcactcc caacgaagac aagatatcct tgatctgtgg atctaccaca cacaaggcta    7260
cttccctgat tggcagaact acacaccagg gccaggatc agatatccac tgacctttgg    7320
atggtgctac aagctagtac cagttgagca agagaaggta gaagaagcca atgaaggaga    7380
gaacacccgc ttgttacacc ctgtgagcct gcatgggatg gatgacccgg agagagaagt    7440
attagagtgg aggtttgaca gccgcctagc atttcatcac atggcccgag agctgcatcc    7500
ggactgtact gggtctctct ggttagacca gatctgagcc tgggagctct ctggctaact    7560
agggaaccca ctgcttaagc ctcaataaag cttgccttga gtgcttcaag tagtgtgtgc    7620
ccgtctgttg tgtgactctg gtaactagag atccctcaga ccctttttagt cagtgtggaa    7680 aatctctagc agggcccgtt taaacccgct gatcagcctc gactgtgcct tctagttgcc    7740
agccatctgt tgtttgcccc tcccccgtgc cttccttgac cctggaaggt gccactccca    7800
ctgtcctttc ctaataaaat gaggaaattg catcgcattg tctgagtagg tgtcattcta    7860
ttctgggggg tggggtgggg caggacagca aggggggagga ttgggaagac aatagcaggc    7920
atgctgggga tgcggtgggc tctatggctt ctgaggcgga agaaccagc tggggctcta    7980 gggggtatcc ccacgcgccc tgtagcggcg cattaagcgc ggcgggtgtg gtggttacgc    8040
```

```
gcagcgtgac cgctacactt gccagcgccc tagcgcccgc tcctttcgct ttcttccctt   8100
cctttctcgc cacgttcgcc ggctttcccc gtcaagctct aaatcggggg ctcccttttag  8160 ggttccgatt tagtgcttta cggcacctcg accccaaaaa acttgattag ggtgatggtt   8220
cacgtagtgg gccatcgccc tgatagacgg ttttcgccc tttgacgttg gagtccacgt    8280
tctttaatag tggactcttg ttccaaactg gaacaacact caaccctatc tcggtctatt   8340
cttttgattt ataagggatt ttgccgattt cggcctattg gttaaaaaat gagctgattt   8400
aacaaaaatt taacgcgaat taattctgtg gaatgtgtgt cagttagggt gtggaaagtc   8460
cccaggctcc ccagcaggca gaagtatgca aagcatgcat ctcaattagt cagcaaccag   8520
gtgtggaaag tccccaggct ccccagcagg cagaagtatg caaagcatgc atctcaatta   8580
gtcagcaacc atagtcccgc ccctaactcc gcccatcccg ccctaactc cgcccagttc    8640 cgcccattct ccgcccatg gctgactaat ttttttatt tatgcagagg ccgaggccgc     8700
ctctgcctct gagctattcc agaagtagtg aggaggcttt tttggaggcc taggcttttg   8760
caaaaagctc ccgggagctt gtatatccat ttcggatct gatcagcacg tgttgacaat    8820
taatcatcgg catagtatat cggcatagta taatacgaca aggtgaggaa ctaaaccatg   8880
gccaagttga ccagtgccgt tccggtgctc accgcgcgcg acgtcgccgg agcggtcgag   8940
ttctggaccg accggctcgg gttctcccgg gacttcgtgg aggacgactt cgccggtgtg   9000
gtccgggacg acgtgaccct gttcatcagc gcggtccagg accaggtggt gccggacaac   9060
accctggcct gggtgtgggt gcgcggcctg gacgagctgt acgccgagtg gtcggaggtc   9120
gtgtccacga acttccggga cgcctccggg ccggccatga ccgagatcgg cgagcagccg   9180
tgggggcggg agttcgccct gcgcgacccg gccggcaact gcgtgcactt cgtggccgag   9240
gagcaggact gacacgtgct acgagatttc gattccaccg ccgccttcta tgaaaggttg   9300
ggcttcggaa tcgttttccg ggacgccggc tggatgatcc tccagcgcgg ggatctcatg   9360
ctggagttct tcgcccaccc caacttgttt attgcagctt ataatggtta caaataaagc   9420
aatagcatca caaatttcac aaataaagca ttttttttcac tgcattctag ttgtggtttg   9480
tccaaactca tcaatgtatc ttatcatgtc tgtataccgt cgacctctag ctagagcttg   9540
gcgtaatcat ggtcatagct gtttcctgtg tgaaattgtt atccgctcac aattccacac   9600
aacatacgag ccggaagcat aaagtgtaaa gcctggggtg cctaatgagt gagctaactc   9660
acattaattg cgttgcgctc actgcccgct ttccagtcgg gaaacctgtc gtgccagctg   9720
cattaatgaa tcggccaacg cgcggggaga ggcggtttgc gtattgggcg ctcttccgct   9780
tcctcgctca ctgactcgct gcgctcggtc gttcggctgc ggcgagcggt atcagctcac   9840
tcaaaggcgg taatacggtt atccacagaa tcagggggata acgcaggaaa gaacatgtga   9900
gcaaaaggcc agcaaaaggc caggaaccgt aaaaaggccg cgttgctggc gttttccat    9960 aggctccgcc cccctgacga gcatcacaaa aatcgacgct caagtcagag gtggcgaaac  10020
ccgacaggac tataaagata ccaggcgttt ccccctggaa gctccctcgt gcgctctcct  10080
gttccgaccc tgccgcttac cggatacctg tccgcctttc tcccttcggg aagcgtggcg  10140
ctttctcata gctcacgctg taggtatctc agttcggtgt aggtcgttcg ctccaagctg  10200
ggctgtgtgc acgaaccccc cgttcagccc gaccgctgcg ccttatccgg taactatcgt  10260
cttgagtcca acccggtaag acacgactta tcgccactgg cagcagccac tggtaacagg  10320
attagcagag cgaggtatgt aggcggtgct acagagttct tgaagtggtg gcctaactac  10380
ggctacacta gaagaacagt atttggtatc tgcgctctgc tgaagccagt taccttcgga  10440
```

| | |
|---|---:|
| aaaagagttg gtagctcttg atccggcaaa caaaccaccg ctggtagcgg tggtttttt | 10500 |
| gtttgcaagc agcagattac gcgcagaaaa aaaggatctc aagaagatcc tttgatcttt | 10560 |
| tctacgggt ctgacgctca gtggaacgaa aactcacgtt aagggatttt ggtcatgaga | 10620 |
| ttatcaaaaa ggatcttcac ctagatcctt ttaaattaaa aatgaagttt taaatcaatc | 10680 |
| taaagtatat atgagtaaac ttggtctgac agttaccaat gcttaatcag tgaggcacct | 10740 |
| atctcagcga tctgtctatt tcgttcatcc atagttgcct gactcccgt cgtgtagata | 10800 |
| actacgatac gggagggctt accatctggc cccagtgctg caatgatacc gcgagaccca | 10860 |
| cgctcaccgg ctccagattt atcagcaata aaccagccag ccggaagggc cgagcgcaga | 10920 |
| agtggtcctg caactttatc cgcctccatc cagtctatta attgttgccg ggaagctaga | 10980 |
| gtaagtagtt cgccagttaa tagtttgcgc aacgttgttg ccattgctac aggcatcgtg | 11040 |
| gtgtcacgct cgtcgtttgg tatggcttca ttcagctccg gttcccaacg atcaaggcga | 11100 |
| gttacatgat cccccatgtt gtgcaaaaaa gcggttagct ccttcggtcc tccgatcgtt | 11160 |
| gtcagaagta agttggccgc agtgttatca ctcatggtta tggcagcact gcataattct | 11220 |
| cttactgtca tgccatccgt aagatgcttt tctgtgactg gtgagtactc aaccaagtca | 11280 |
| ttctgagaat agtgtatgcg gcgaccgagt tgctcttgcc cggcgtcaat acgggataat | 11340 |
| accgcgccac atagcagaac tttaaaagtg ctcatcattg gaaaacgttc ttcggggcga | 11400 |
| aaactctcaa ggatcttacc gctgttgaga tccagttcga tgtaacccac tcgtgcaccc | 11460 |
| aactgatctt cagcatcttt tactttcacc agcgtttctg ggtgagcaaa aacaggaagg | 11520 |
| caaaatgccg caaaaaaggg aataagggcg acacggaaat gttgaatact catactcttc | 11580 |
| cttttttcaat attattgaag catttatcag ggttattgtc tcatgagcgg atacatattt | 11640 |
| gaatgtattt agaaaaataa acaaataggg gttccgcgca catttccccg aaaagtgcca | 11700 |
| cctgac | 11706 |

<210> SEQ ID NO 14
<211> LENGTH: 7886
<212> TYPE: DNA
<213> ORGANISM: Artificial
<220> FEATURE:
<223> OTHER INFORMATION: Synthetic construct

<400> SEQUENCE: 14

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtttaac attatggcct taggtcactt | 180 |
| catctccatg gggttcttct tctgattttc tagaaaatga gatgggggtg cagagagctt | 240 |
| cctcagtgac ctgcccaggg tcacatcaga aatgtcagag ctagaacttg aactcagatt | 300 |
| actaatctta aattccatgc cttggggca tgcaagtacg atatacagaa ggagtgaact | 360 |
| cattagggca gatgaccaat gagtttagga aagaagagtc cagggcaggg tacatctaca | 420 |
| ccacccgccc agccctgggt gagtccagcc acgttcacct cattatagtt gcctctctcc | 480 |
| agtcctacct tgacgggaag cacaagcaga aactgggaca ggagcccag gagaccaaat | 540 |
| cttcatggtc cctctgggag gatgggtggg gagagctgtg gcagaggcct caggaggggc | 600 |
| cctgctgctc agtggtgaca gataggggtg agaaagcaga cagagtcatt ccgtcagcat | 660 |
| tctgggtctg tttggtactt cttctcacgc taaggtggcg gtgtgatatg cacaatggct | 720 |

```
aaaaagcagg gagagctgga aagaaacaag gacagagaca gaggccaagt caaccagacc      780
aattcccaga ggaagcaaag aaaccattac agagactaca aggggggaagg gaaggagaga    840 tgaattagct tcccctgtaa accttagaac ccagctgttg ccagggcaac ggggcaatac     900
ctgtctcttc agaggagatg aagttgccag ggtaactaca tcctgtcttt ctcaaggacc     960
atcccagaat gtggcaccca ctagccgtta ccatagcaac tgcctctttg ccccacttaa    1020
tcccatcccg tctgttaaaa gggccctata gttggaggtg ggggaggtag gaagagcgat    1080
gatcacttgt ggactaagtt tgttcgcatc cccttctcca accccctcag tacatcaccc    1140
tgggggaaca gggtccactt gctcctgggc ccacacagtc ctgcagtatt gtgtatataa    1200
ggccagggca aagaggagca ggttttaaag tgaaaggcag gcaggtgttg gggaggcagt    1260
taccggggca acgggaacag ggcgtttcgg aggtggttgc catggggacc tggatgctga    1320
cgaaggctcg cgaggctgtg agcagccaca gtgccctgct cagaagcccc aagctcgtca    1380
gtcaagccgg ttctccgttt gcactcagga gcacgggcag gcgagtggcc cctagttctg    1440
ggggcagctc tagagcggta ccggatccat gacagagacc ctgcctcccg tgaccgagag    1500
tgccgtggcc cttcaagccg aggttaccca aagggagttg ttcgagttcg tgctgaacga    1560
cccctttgct tgcaagcagtc tctatatcaa catcgcactt gcaggactga gtatactgct    1620
gttcgttttt atgacccgag gactcgatga tccacgggca aaacttattg ctgtgtcaac    1680
catccttgtg cctgtcgtca gcattgcctc ctacactgga ttggcgagcg gcctgacaat    1740
ttccgttctt gaaatgccag cgggccattt tgcagaaggc agctcagtga tgctgggagg    1800
agaagaggta gatggtgtag tcaccatgtg gggacggtat ctcacctggg cactttccac    1860
gcccatgatt ctcctcgctc tgggtctcct ggccggaagc aatgctacaa agctcttcac    1920
agctatcact ttcgatatcg ctatgtgcgt gactggcctt gccgcggccc tgactacctc    1980
ctcccacctc atgagatggt tctggtacgc tatcagttgt gcatgctttc tggtggtctt    2040
gtatatcctg ctggtggagt gggcacagga cgccaaagcc gcgggaaccg ctgacatgtt    2100
caataccctg aagctgttga cagtagtgat gtggctgggg tatccaattg tgtgggctct    2160
tggagtcgag ggtatcgcgg tgttgcccgt tggggtgacg agctgggat attcttttcct    2220 ggatatcgtg gcaaagtaca ttttcgcatt cttgctcctg aactatctga cgtcaaacga    2280
atctgtcgtg tccggcagca ttttggatgt tccatctgct tctgggaccc cggctgatga    2340
tgcggccgca gtgagcaagg gcgaggagct gttcaccggg gtggtgccca tcctggtcga    2400 gctgacggc gacgtaaacg gccacaagtt cagcgtgtcc ggcgagggcg agggcgatgc    2460
cacctacggc aagctgaccc tgaagctgat ctgcaccacc ggcaagctgc ccgtgccctg    2520 gcccacccte gtgaccaccc tgggctacgg cctgcagtgc ttcgcccgct accccgacca    2580
catgaagcag cacgacttct tcaagtccgc catgcccgaa ggctacgtcc aggagcgcac    2640
catcttcttc aaggacgacg gcaactacaa gacccgcgcc gaggtgaagt tcgagggcga    2700
caccctggtg aaccgcatcg agctgaaggg catcgacttc aaggaggacg gcaacatcct    2760
ggggcacaag ctggagtaca actacaacag ccacaacgtc tatatcaccg ccgacaagca    2820
gaagaacggc atcaaggcca acttcaagat ccgccacaac atcgaggacg gcggcgtgca    2880
gctcgccgac cactaccagc agaacacccc catcggcgac ggccccgtgc tgctgcccga    2940
caaccactac ctgagctacc agtccaagct gagcaaagac cccaacgaga agcgcgatca    3000
catggtcctg ctggagttcg tgaccgccgc cgggggtacc aaggtgtacg accccgcagca   3060 gaggaagagg atgatcaccg ccccccagtg gtgggccagg tgcaagcaga tgaacgtgct    3120
```

```
ggacagcttc atcaactact acgacagcga gaagcacgcc gagaacgccg tgatcttcct    3180
gcacggcaac gccactagca gctacctgtg gaggcacgtg gtgccccaca tcgagcccgt    3240
ggccaggtgc atcatccccg atctgatcgg catgggcaag agcggcaaga gcggcaacgg    3300
cagctacagg ctgctggacc actacaagta cctgaccgcc tggttcgagc ttctgaacct    3360
gcccaagaag atcatcttcg tgggccacga ctggggcgcc gccctggcct tccactacgc    3420
ctacgagcac caggacagga tcaaggccat cgtgcacatg gagagcgtgg tggacgtgat    3480
cgagagctgg gacgagtggc cagacatcga ggaggacatc gccctgatca gagcgagga    3540 gggcgagaag atggtgctgg agaacaactt cttcgtggag accgtgctgc ccagcaagat    3600
catgagaaag ctggagcccg aggagttcgc cgcctacctg agcccttca aggagaaggg    3660 cgaggtgaga agaccaccc tgagctggcc cagagagatc cccctggtga agggcggcaa    3720
gcccgacgtg gtgcagatcg tgagaaacta caacgcctac ctgagagcca gcgacgacct    3780
gcccaagctg ttcatcgagg gcgacccccg cttcttcagc aacgccatcg tggagggcgc    3840
caagaagttc cccaacaccg agttcgtgaa ggtgaagggc ctgcacttcc tccaggagga    3900
cgcccccgac gagatgggca gtacatcaa gagcttcgtg gagagagtgc tgaagaacga    3960
gcagttctgc tacgagaacg aggtgtaaga attcgatatc aagcttatcg ataatcaacc    4020
tctggattac aaaatttgtg aaagattgac tggtattctt aactatgttg ctccttttac    4080
gctatgtgga tacgctgctt taatgccttt gtatcatgct attgcttccc gtatggcttt    4140
cattttctcc tccttgtata atcctggtt gctgtctctt tatgaggagt tgtggcccgt    4200
tgtcaggcaa cgtggcgtgg tgtgcactgt gtttgctgac gcaaccccca ctggttgggg    4260
cattgccacc acctgtcagc tcctttccgg gactttcgct ttcccctcc ctattgccac    4320 ggcggaactc atcgccgcct gccttgcccg ctgctggaca ggggctcggc tgttgggcac    4380
tgacaattcc gtggtgttgt cggggaaatc atcgtccttt ccttggctgc tcgcctgtgt    4440
tgccacctgg attctgcgcg gacgtccttc tgctacgtc ccttcggccc tcaatccagc    4500
ggaccttcct tcccgcggcc tgctgccggc tctgcggcct cttccgcgtc ttcgccttcg    4560
ccctcagacg agtcggatct ccctttgggc cgcctcccg catcgatacc gagcgctgct    4620
cgagagatct acgggtggca tccctgtgac ccctccccag tgcctctcct ggccctggaa    4680
gttgccactc cagtgcccac cagccttgtc ctaataaaat taagttgcat catttttgtct    4740 gactaggtgt ccttctataa tattatgggg tggaggggg tggtatggag caagggcaa    4800 gttgggaaga caacctgtag ggcctgcggg gtctattggg aaccaagctg gagtgcagtg    4860
gcacaatctt ggctcactgc aatctccgcc tcctgggttc aagcgattct cctgcctcag    4920
cctcccgagt tgttgggatt ccaggcatgc atgaccaggc tcagctaatt tttgtttttt    4980
tggtagagac ggggtttcac catattggcc aggctggtct ccaactccta atctcaggtg    5040
atctacccac cttggcctcc caaattgctg gattacagg cgtgaaccac tgctcccttc    5100
cctgtccttc tgattttgta ggtaaccacg tgcggaccga gcggccgcag gaaccctag    5160 tgatggagtt ggccactccc tctctgcgcg ctcgctcgct cactgaggcc gggcgaccaa    5220
aggtcgcccg acgcccgggc tttgcccggg cggcctcagt gagcgagcga gcgcgcagct    5280
gcctgcaggg gcgcctgatg cggtattttc tccttacgca tctgtgcggt atttcacacc    5340
gcatacgtca aagcaaccat agtacgcgcc ctgtagcggc gcattaagcg cggcgggtgt    5400
ggtggttacg cgcagcgtga ccgctacact tgccagcgcc ctagcgcccg ctcctttcgc    5460
```

```
tttcttcccct tcctttctcg ccacgttcgc cggctttccc cgtcaagctc taaatcgggg   5520
gctcccttta gggttccgat ttagtgcttt acggcacctc gacccaaaa aacttgattt    5580
gggtgatggt tcacgtagtg ggccatcgcc ctgatagacg ttttttcgcc ctttgacgtt   5640
ggagtccacg ttctttaata gtggactctt gttccaaact ggaacaacac tcaaccctat   5700
ctcgggctat tcttttgatt tataagggat tttgccgatt tcggcctatt ggttaaaaaa   5760
tgagctgatt taacaaaaat ttaacgcgaa ttttaacaaa atattaacgt ttacaatttt   5820
atggtgcact ctcagtacaa tctgctctga tgccgcatag ttaagccagc cccgacaccc   5880
gccaacaccc gctgacgcgc cctgacgggc ttgtctgctc ccggcatccg cttacagaca   5940
agctgtgacc gtctccggga gctgcatgtg tcagaggttt tcaccgtcat caccgaaacg   6000
cgcgagacga aagggcctcg tgatacgcct atttttatag gttaatgtca tgataataat   6060
ggtttcttag acgtcaggtg gcacttttcg gggaaatgtg cgcggaaccc ctatttgttt   6120
atttttctaa atacattcaa atatgtatcc gctcatgaga caataaccct gataaatgct   6180
tcaataatat tgaaaaagga agagtatgag tattcaacat ttccgtgtcg cccttattcc   6240
cttttttgcg gcattttgcc ttcctgtttt tgctcaccca gaaacgctgg tgaaagtaaa   6300
agatgctgaa gatcagttgg gtgcacgagt gggttacatc gaactggatc tcaacagcgg   6360
taagatcctt gagagttttc gccccgaaga acgttttcca atgatgagca cttttaaagt   6420
tctgctatgt ggcgcggtat tatcccgtat tgacgccggg caagagcaac tcggtcgccg   6480
catacactat tctcagaatg acttggttga gtactcacca gtcacagaaa agcatcttac   6540
ggatggcatg acagtaagag aattatgcag tgctgccata accatgagtg ataacactgc   6600
ggccaactta cttctgacaa cgatcggagg accgaaggag ctaaccgctt ttttgcacaa   6660
catgggggat catgtaactc gccttgatcg ttgggaaccg gagctgaatg aagccatacc   6720
aaacgacgag cgtgacacca cgatgcctgt agcaatggca acaacgttgc gcaaactatt   6780
aactggcgaa ctacttactc tagcttcccg gcaacaatta atagactgga tggaggcgga   6840
taaagttgca ggaccacttc tgcgctcggc ccttccggct ggctggttta ttgctgataa   6900
atctggagcc ggtgagcgtg gtctcgcgg tatcattgca gcactggggc cagatggtaa   6960
gccctcccgt atcgtagtta tctacacgac ggggagtcag gcaactatgg atgaacgaaa   7020
tagacagatc gctgagatag gtgcctcact gattaagcat tggtaactgt cagaccaagt   7080
ttactcatat atactttaga ttgatttaaa acttcatttt taatttaaaa ggatctaggt   7140
gaagatcctt tttgataatc tcatgaccaa atcccttaa cgtgagtttt cgttccactg    7200
agcgtcagac cccgtagaaa agatcaaagg atcttcttga gatcctttt ttctgcgcgt     7260
aatctgctgc ttgcaaacaa aaaaaccacc gctaccagcg gtggtttgtt tgccggatca   7320
agagctacca actctttttc cgaaggtaac tggcttcagc agagcgcaga taccaaatac   7380
tgtccttcta gtgtagccgt agttaggcca ccacttcaag aactctgtag caccgcctac   7440
atacctcgct ctgctaatcc tgttaccagt ggctgctgcc agtggcgata agtcgtgtct   7500
taccgggttg gactcaagac gatagttacc ggataaggcg cagcggtcgg gctgaacggg   7560
gggttcgtgc acacagccca gcttggagcg aacgacctac accgaactga gatacctaca   7620
gcgtgagcta tgagaaagcg ccacgcttcc cgaagggaga aaggcggaca ggtatccggt   7680
aagcggcagg gtcggaacag gagagcgcac gagggagctt ccagggggaa acgcctggta   7740
tctttatagt cctgtcgggt ttcgccacct ctgacttgag cgtcgatttt tgtgatgctc   7800
gtcagggggg cggagcctat ggaaaaacgc cagcaacgcg gcctttttac ggttcctggc   7860
```

```
cttttgctgg cctttttgctc acatgt                                    7886
```

<210> SEQ ID NO 15
<211> LENGTH: 6
<212> TYPE: PRT
<213> ORGANISM: Artificial
<220> FEATURE:
<223> OTHER INFORMATION: Synthetic construct

<400> SEQUENCE: 15

Gly Gly Gly Gly Gly Gly
1               5

<210> SEQ ID NO 16
<211> LENGTH: 5
<212> TYPE: PRT
<213> ORGANISM: Artificial
<220> FEATURE:
<223> OTHER INFORMATION: Synthetic construct

<400> SEQUENCE: 16

Gly Gly Gly Gly Thr
1               5

<210> SEQ ID NO 17
<211> LENGTH: 6
<212> TYPE: PRT
<213> ORGANISM: Artificial
<220> FEATURE:
<223> OTHER INFORMATION: Synthetic construct

<400> SEQUENCE: 17

Gly Gly Gly Pro Pro Pro
1               5

<210> SEQ ID NO 18
<211> LENGTH: 7
<212> TYPE: PRT
<213> ORGANISM: Artificial
<220> FEATURE:
<223> OTHER INFORMATION: Synthetic construct

<400> SEQUENCE: 18

Gly Gly Gly Ala Pro Pro Pro
1               5

OPTOGENETIC INHIBITION OF OVERACTIVE NEURONAL ACTIVITY

CROSS-REFERENCE TO RELATED APPLICATIONS

This application is a division of U.S. patent application Ser. No. 14/529,539 filed Oct. 31, 2014 that granted as U.S. Pat. No. 9,926,359 on Mar. 27, 2018, which claims the benefit of U.S. Provisional Application No. 61/908,964 filed Nov. 26, 2013. The entirety of each of these applications is hereby incorporated by reference for all purposes.

STATEMENT REGARDING FEDERALLY FUNDED RESEARCH

This invention was made with government support under grants NS079268 and NS079757 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 10206USDIV_ST25.txt. The text file is 89 KB, was created on Aug. 19, 2020, and is being submitted electronically via EFS-Web.

BACKGROUND

Approximately 20-40% of patients with epilepsy have refractory seizures unresponsive to pharmacotherapy. Thus, there is a need to develop alternative treatments for this large population of people who are at higher risk of developing epilepsy-related disabilities.

Halorhodopsin is a membrane bound light-gated ion pump. Upon exposure to light, halorhodopsin moves chloride ions into a cell. Light induced halorhodopsin silences excitable neuronal cells. Zhao et al. reported the halorhodopsin from halophilic bacterium *Natronobacterium pharaonis* (NpHR) for light-induced silencing of neuronal activity. Brain Cell Biol, 2008, 36(1-4): 141-154. See also Zhang et al., Multimodal fast optical interrogation of neural circuitry. Nature, 2007, 446:633-639.

Luciferases produce light in the presence of luciferin. Coelenterazine (CTZ) is a substrate luciferin of *Renilla reniformis* luciferase (Rluc) and *Gaussia* luciferase (Gluc). Berglund et al. report using a luciferase for light-activating a channel rhodopsin for combined optogenetic and chemical-genetic control of neurons. PLoS ONE, 2013, 8(3): e59759. See also WO 2011/005978 and WO 2010/011404.

References cited herein are not an admission of prior art.

SUMMARY

This disclosure relates to recombinant proteins, vectors, and methods of treating neurological conditions by exposing neurons to an opsin and luciferase in the presence of a luciferin. In certain embodiments, the disclosure relates to treating or preventing epilepsy or seizures comprising administering an effective amount of a nucleic acid or vector that encodes an opsin and luciferase in combination with a luciferin to a subject in need thereof.

In certain embodiments, the disclosure relates to recombinant proteins comprising a light-activated opsin, termed Biologic Controller (BC), and a luciferase and typically comprising a second fluorescent sequence inserted between the C-terminal of the light-activated opsin and N-terminal of the luciferase. Typically the second fluorescent sequence is configured and capable of fluorescence resonance energy transfer (FRET) with the luciferase. In certain embodiments, the luciferase is activity-dependent (e.g. calcium-sensing), termed an Autonomous Biologic Controller (ABC).

In certain embodiments, the recombinant protein comprises SEQ ID NO: 1 or 11 or variant thereof having greater than 50, 60, 70, 80, 90, 95, 98 or 99% identity or similarity thereto. In certain embodiments, the light-activated opsin is halorhodopsin (NpHR), or an enhanced halorhodopsin (eNpHR2.0 and eNpHR3.0). In certain embodiments, the light-activated opsin is archaerhodopsin. In certain embodiments the luciferase is *Renilla* luciferase or *Gaussia* luciferase.

In certain embodiments, the disclosure relates to synthetic nucleic acids or vectors comprising a recombinant nucleic acid encoding a light-activated opsin and encoding a luciferase. In certain embodiments, the vector is a lentiviral vector, adenovirus, retrovirus, an adeno-associated virus (AAV), vaccinia virus, or poxvirus. In certain embodiments, the vector is a herpes simplex virus, e.g., HSV-1. Viral vectors may or may not be deficient or attenuated in their ability to replicate.

In certain embodiments, the light-activated opsin and the luciferase are encoded such that they would be expressed in the same polypeptide.

In certain embodiments, the light-activated opsin and the luciferase are encoded such that they would be expressed in different polypeptides.

In certain embodiments, the synthetic nucleic acid or vector encodes a polypeptide comprising SEQ ID NO: 1 or 11 or variant thereof having greater than 50, 60, 70, 80, 90, 95, 98, or 99% identity or similarity thereto.

In certain embodiments, the synthetic nucleic acid or vector comprises a c-fos promoter.

In certain embodiments, the luciferase is activity-dependent (e.g. responsive to calcium or chloride).

In certain embodiments, the disclosure relates to cells or other expression systems comprising nucleic acids and vectors disclosure herein.

In certain embodiments, the disclosure relates to methods of treating or preventing a neurological disease or condition comprising administering an effective amount of a nucleic acid or vector disclosed herein in combination with a luciferin to a subject in need thereof.

In certain embodiments, the neurological disease is epilepsy, retinal degeneration, Parkinson's disease, or cardiac dysthymias.

In certain embodiments, the neurological condition is a seizure.

In certain embodiments, the luciferin is coelenterazine (CTZ) or derivative.

In certain embodiments, the subject is a human.

In certain embodiments the disclosure relates to recombinant or synthetic peptides, fusions, nucleic acids, or vectors comprising nucleic acid sequences discloses herein or variants thereof having greater than 50, 60, 70, 80, 90, 95, 98, or 99% identity or similarity thereto.

calcium influx) and activate a coupled opsin (Halorhodopsin). The luciferase and opsin are expressed separately (as illustrated in different neurons in this case, although it could also be in the same neuron). Propagating activity induces a Ca influx (1). A Ca-sensing luciferase (2) emits light in response to influx and activates an inhibitory opsin (3), which hyperpolarizes the downstream cell and prevents propagation of pathological activity (4). A calcium-sensitive luciferase senses pathological activity and responds by emitting light, thus activating an inhibitory opsin and arresting propagation of neural activity as the cell is hyperpolarized. Since the bioluminescence is tied to neural activity, as the latter decreases so will the former, as well as the consequent inhibition.

Figure 1A:
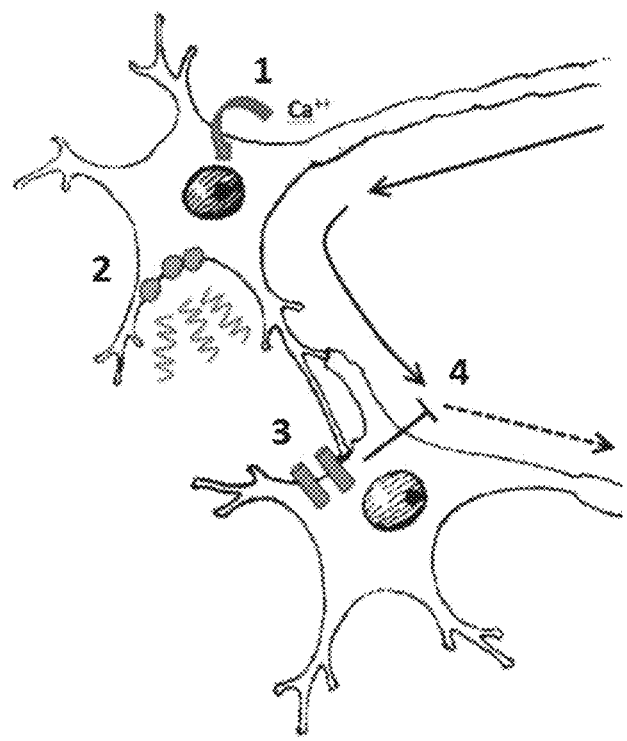
FIG. 1A illustrates an epileptic thermostat by showing how luciferase can be activated by neural activity (e.g.
Figure 1B:
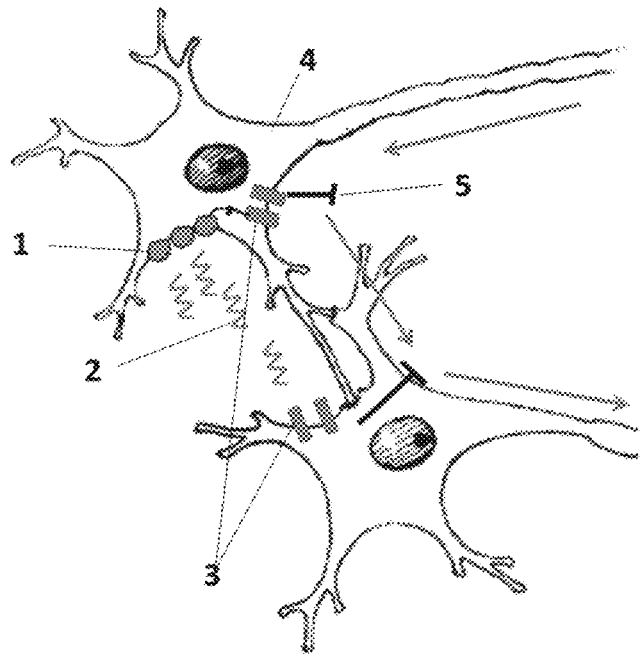

FIG. 1B illustrates a genetically-encoded light-activated opsin, e.g., halorhodopsin (NpHR), enhanced halorhodopsin (eNpHR2.0 and eNpHR3.0), or archaerhodopsin (Arch) (3) fused to a bioluminescent protein, e.g., luciferase (1). The luciferase and opsin are expressed together as a fusion protein. A fluorescent tag (5), e.g, TagBFP-TagGFP2 or EYFP, may also be conjugated to the fusion. See Subach et al. Conversion of Red Fluorescent Protein into a Bright Blue Probe. Chem Biol. 2008; 15 (10):1116-24.

Figure 2:
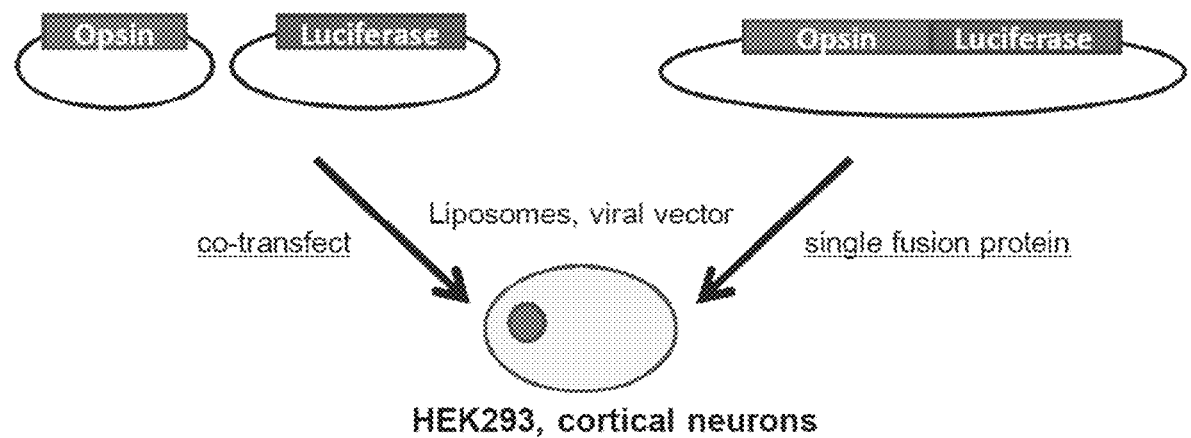

FIG. 2 illustrates Biologic Controllers (BC): BC1.0, Halorhodopsin and TagFPRluc; BC1.1, Halorhodopsin fused to TagFPRluc; BC2.0, Arch and TagFPRluc; BC2.1, Arch fused to TagFPRluc.

Figure 3A:
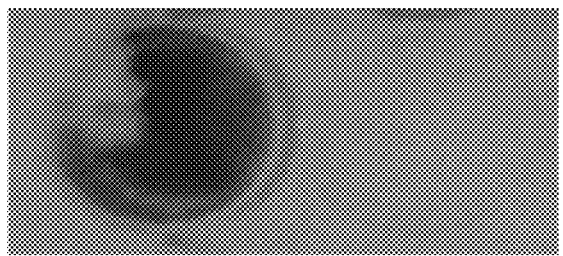

FIG. 3A shows transfected HEK293 cells express BC1.0 Biologic Controllers luminesce (black signal) after addition of CTZ.

Figure 3B:
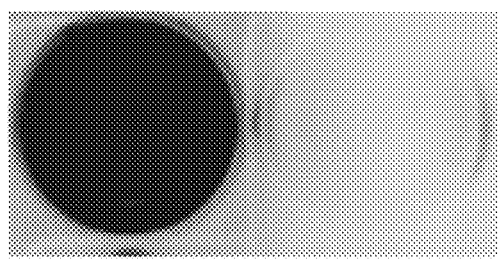

FIG. 3B shows transfected HEK293 cells express BC1.1 Biologic Controllers luminesce (black signal) after addition of CTZ.

Figure 4:
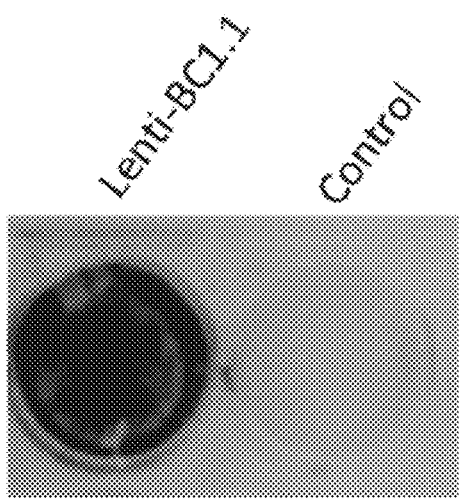

FIG. 4 illustrates Biologic Controller 1.1 was packaged into a lentiviral vector and used to infect dissociated cortical neurons. Infected neurons still luminesce (black signal) after addition of CTZ and hyperpolarize in response to green light illumination.

Figure 5:
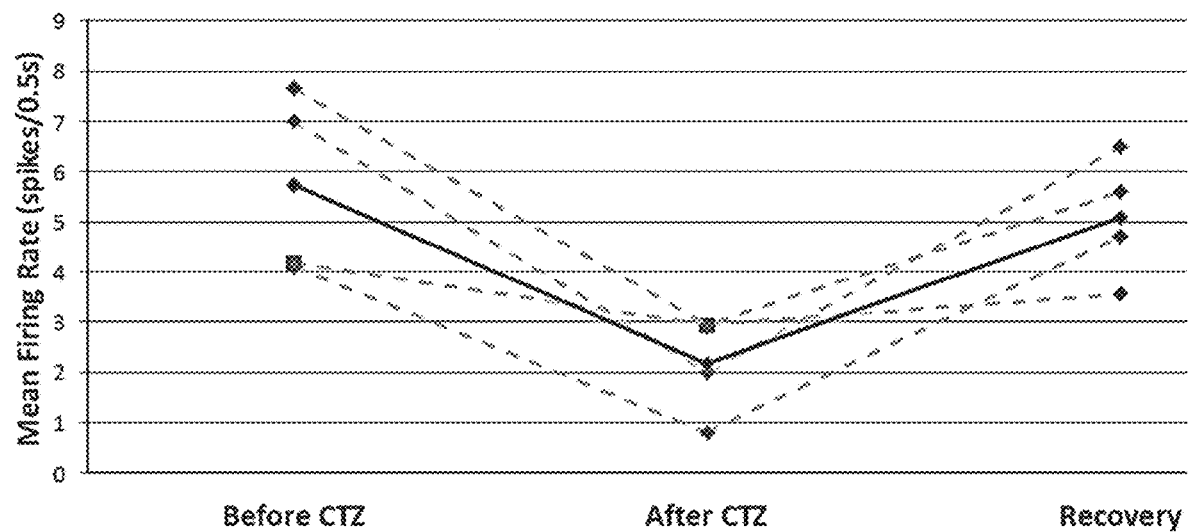

FIG. 5 shows data indicating Biologic Controller 1.1 was able to inhibit evoked activity in cortical neuron cultures. Trains of action potentials were evoked by 30 pA current injections. (A): Firing rate was significantly reduced during periods of green light illumination. (B): Firing rate was similarly reduced after CTZ addition. (C): Baseline activity was eventually recovered minutes after CTZ addition. CTZ did not have any significant effect on firing rate in control (uninfected) neurons.

Figure 6A:
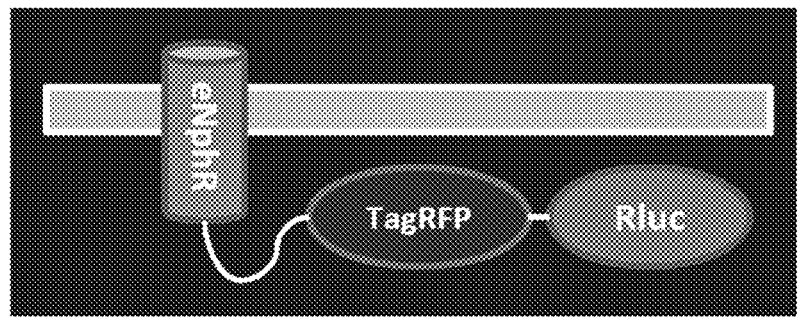

FIG. 6A illustrates an embodiment of the disclosure.

Figure 6B:
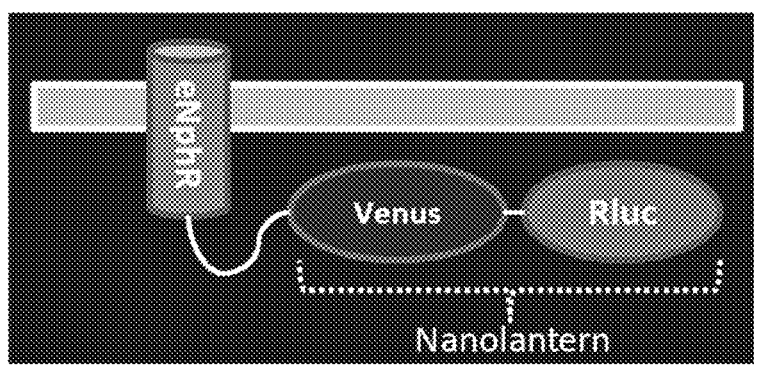

FIG. 6B illustrates an embodiment of the disclosure.

Figure 7A:
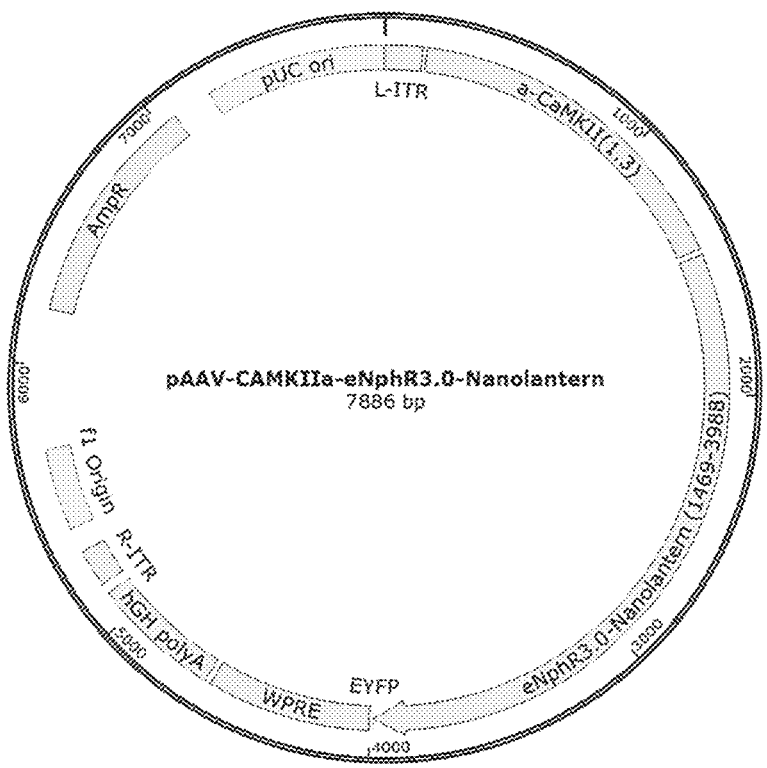

FIG. 7A illustrates a vector map for pAAV-CAMKIIa-eNphR3.0-Nanolantern.

Figure 7B:
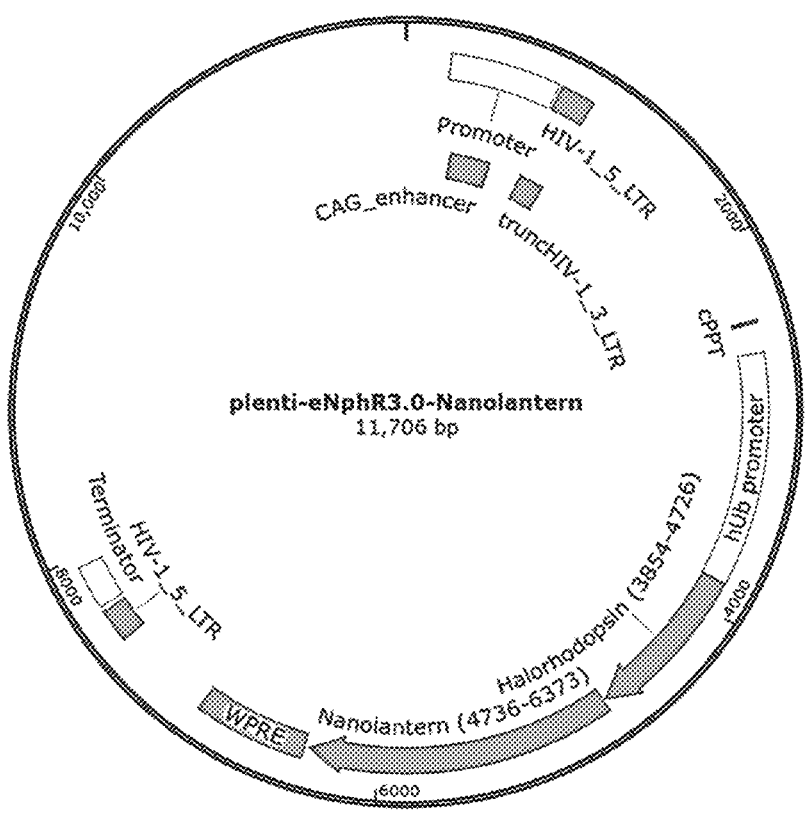

FIG. 7B illustrates a vector map for plenti-eNphR3.0-Nanolantern.

Figure 7C:
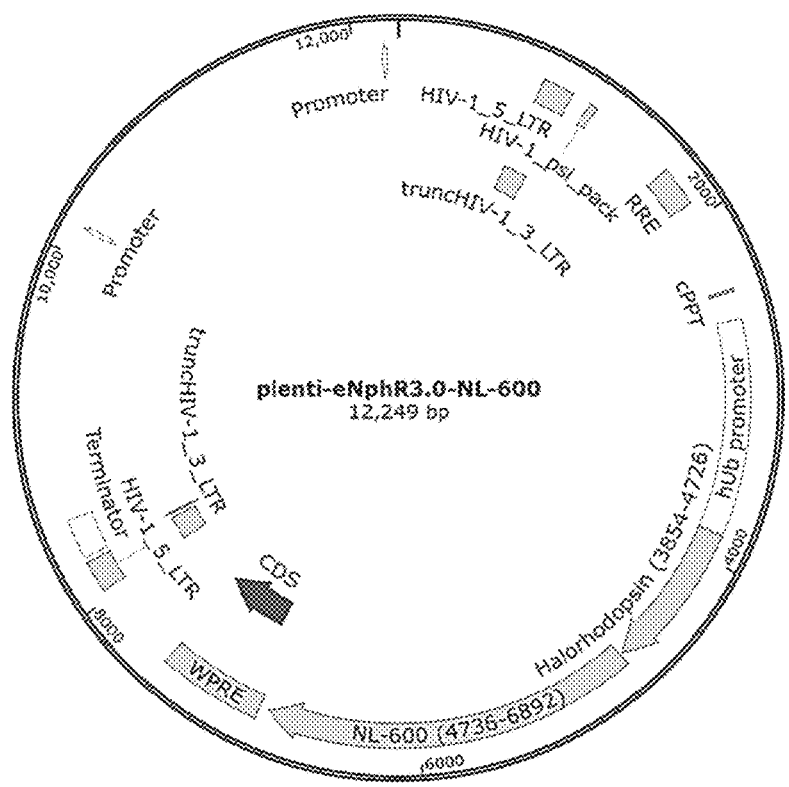

FIG. 7C illustrates a vector map for plenti-eNphR3.0-NL-600.

Figure 8:
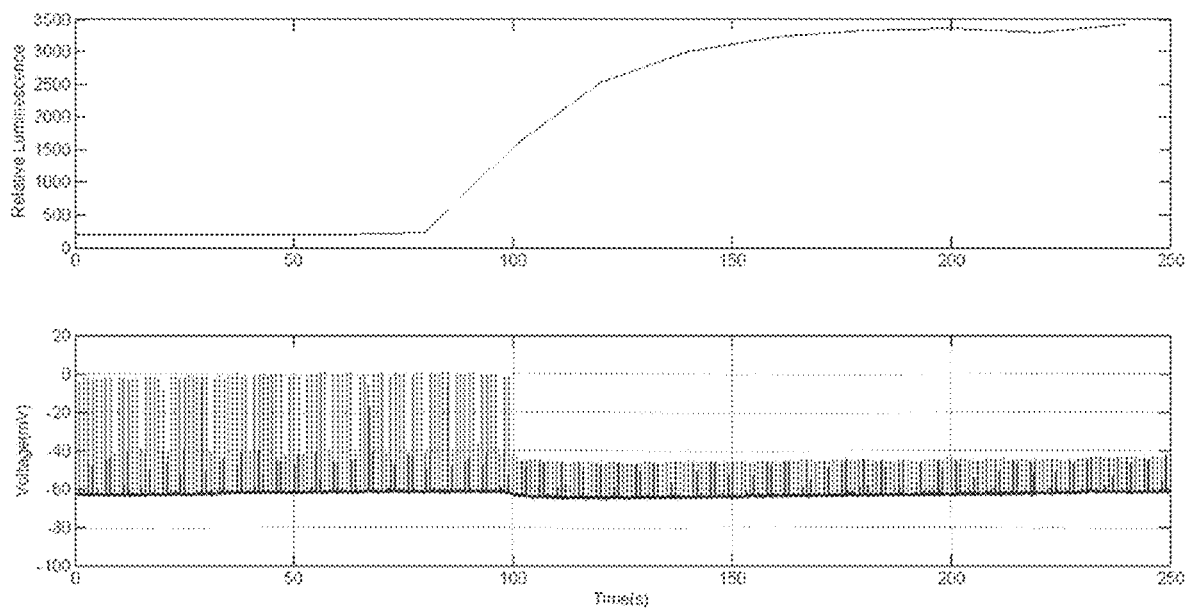

FIG. 8 shows data indicating the inhibition of evoked spikes in a neuron expressing eNpHR3.0-Nanolantern. When a neuron is given a sub-threshold depolarizing current injection (not every current injection induces an action potential), CTZ is able to completely attenuate evoked action potentials. This inhibition of evoked activity corresponds to an increase in luminescence signal (top).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug.

It must be noted that, as used in the specification and the appended claims, the singular forms "a," "an," and "the" include plural referents unless the context clearly dictates otherwise.

The term "opsin" refers to light-sensitive membrane-bound channel polypeptides typically of 35-55 kDa. Examples include halorhodopsin (NpHR), or enhanced halorhodopsins (eNpHR2.0 and eNpHR3.0), archaerhodopsin, and variants thereof.

An example halorhodopsin (eNpHR2.0) has the following sequence (SEQ ID NO: 5), MTETLPPVTESAV-ALQAEVTQRELFEFVLNDPLLASSLYINIALAGLSILL-FVFMTRGLDD PRAKLIAVSTILVPVVSIASYT-GLASGLTISVLEMPAGHFAEGSSVMLGGEEVDG VVTM WGRYLTWALSTPMILLALGLLAG-SNATKLFTAITFDIAMCVTGLAAALTTSSHLMRWF WYAISCACFLVVLYILLVEWAQDA-KAAGTADMFNTLKLLTVVMWLGYPIVWALGVEG IAVLPVGVTSWGYSFLDIVAKYIFAFLLLNYLTS-NESVVSGSILDVPSASGTPADD An example halorhodopsin (eNpHR3.0) has the following sequence (SEQ ID NO: 6). MTETLPPVTESAV- ALQAEVTQRELFEFVLNDPLLASSLYINIALAGLSILL- FVFMTRGLDD PRAKLIAVSTILVPVVSIASYT- GLASGLTISVLEMPAGHFAEGSSVMLGGEEVDGVVTM WGRYLTWALSTPMILLALGLLAGSNATKLFTAITFDI- AMCVTGLAAALTTSSHLMRWF WYAIS- CACFLVVLYILLVEWAQDA- KAAGTADMFNTLKLLTVVMWLGYPIVWALGVEG IAVLPVGVTSWGYSFLDIVAKYIFAFLLLNYLTS- NESVVSGSILDVPSASGTPADD Contemplated variants may have greater than 50, 60, 70, 80, 90, 95, 98 or 99% identity or similarity thereto.

An example archaerhodopsin has the following sequence (SEQ ID NO: 7), MDPIALQAGY DLLGDGRPET LWL- GIGTLLM LIGTFYFIVK GWGVTDKEAR EYYSITILVP GIASAAYLSM FFGIGLTEVT VAGEVLDIYY ARY- ADWLFTT PLLLLDLALL AKVDRVSIGT LVGVDALMIV TGLIGALSHT PLARYSWWLF STICMIVVLY FLATSLRAAA KERGPEVAST FNTL- TALVLV LWTAYPILWI IGTEGAGVVG LGIETLLFMV LDVTAKVGFG FILLRSRAIL GDTEAPEP. Contemplated variants may have greater than 50, 60, 70, 80, 90, 95, 98 or 99% identity or similarity thereto.

The term "luciferase" refers to luciferin oxidative enzymes that function in bioluminescence. Luciferin refers to a compound that emits light due to a reaction with a luciferase. Coelenterazine and water soluble derivatives are known luciferins. A luciferase may be naturally occurring or a non-naturally occurring variant. Examples include *Renilla reniformis* luciferase, *Gaussia* luciferase, aequorin, firefly luciferase, Metridia luciferase (MetLuc) and variants thereof. An example Luciferase is RLuc8 has the following sequence (SEQ ID NO: 8) MASKVYDPEQ RKR- MITGPQW WARCKQMNVL DSFINYYDSE KHAE- NAVIFL HGNATSSYLW RHVVPHIEPV ARCIIPDLIG MGKSGKSGNG SYRLLDHYKY LTAWFELLNL PKKIIFVGHD WGAALAFHYA YEHQDRIKAI VHMESVVDVI ESWDEWPDIE EDIALIKSEE GEKMVLENNF FVETVLPSKI MRKLEPEEFA AYLEPFKEKG EVRRPTLSWP REIPLVKGGK PDVVQI- VRNY NAYLRASDDL PKLFIESDPG FFSNAIVEGA KKFPNTEFVK VKGLHFLQED APDEMGKYIK SFVERVLKNE Q. See Loening et al., Consensus guided mutagenesis of *Renilla* luciferase yields enhanced stability and light output. Prot. Eng. Des. Sel. 19, 391-400 (2006). Contemplated variants may have greater than 50, 60, 70, 80, 90, 95, 98 or 99% identity or similarity thereto.

A "fluorescent protein" refers to a polypeptide that upon expression maintains fluorescence upon exposure to light. The fluorescent protein may contain multiple or repeating sequences. Multiple sequences may be FRET pairs. Examples include yellow fluorescent protein and variants thereof such as yellow fluorescent protein (YFP) having mutation F46L and optionally other mutations, F64L, M153T, V163A, and/or S175G. See Nagai et al. A variant of yellow fluorescent protein with fast and efficient maturation for cell-biological applications. Nat. Biotechnol. 20, 87-90 (2002). An example YFP has the following sequence (SEQ ID NO: 9), MSKGEELFTG VVPILVELDG DVNGHKFSVS GEGEGDATYG KLTLKFICTT GKLPVPWPTL VTTFGYGLQC FARYPDHMKR HDFFKSAMPE GYVQERTIFF KDDGNYKTRA EVKFEGDTLV NRIELKGIDF KEDGNILGHK LEYNYNSHNV YIMADKQKNG IKVNFKIRHN IEDGSVQLAD HYQQNTPIGD GPVLLPDNHY LSYQSALSKD PNEKRDHMVL LEFVTAAGIT HGMDELYK. Contemplated variants may have greater than 50, 60, 70, 80, 90, 95, 98 or 99% identity or similarity thereto. "Venus" refers to a YFP variant having the following sequence (SEQ ID NO: 10) MVSKG EELFTGVVPI LVELDGDVNG HKFSVSGEGE GDATYGKLTL KLICTTGKLP VPWPTLVTTL GYGLQCFARY PDHMKQHDFF KSAMPEGYVQ ERTIFFKDDG NYKTRAEVKF EGDTLVNRIE LKGIDFKEDG NILGHKLEYN YNSHNVYITA DKQKNGIKAN FKIRHNIEDG GVQLADHYQQ NTPIGDGPVL LPDN- HYLSYQ SALSKDPNEK RDHMVLLEFV TAAGITLGMD ELYK.

The term "a nucleic acid sequence encoding" a specified polypeptide refers to a nucleic acid sequence comprising the coding region of a gene or in other words the nucleic acid sequence which encodes a gene product. The coding region may be present in either a cDNA, synthetic copy or genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene.

Efficient expression of recombinant nucleic acid sequences in eukaryotic cells requires expression of signals directing the efficient termination and polyadenylation of the resulting transcript. Transcription termination signals are generally found downstream of the polyadenylation signal and are typically a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene.

Sequence "identity" refers to the number of exactly matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example the polypeptides GGGGGG (SEQ ID NO: 15) and GGGGT (SEQ ID NO: 16) have a sequence identity of 4 out of 5 or 80%. For example, the polypeptides GGGPPP (SEQ ID NO: 17) and GGGAPPP (SEQ ID NO: 18) have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing an amino group with a hydroxyl group. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

Optogenetic Vectors Using Bioluminescent Light Sources

Light sensitive ion channels or pumps (opsins), when transduced into neural tissue, provide a means to selectively excite or inhibit cell-type specific subpopulations of neurons in vivo. Channelrhodopsin-2 (ChR2) is a cation channel that is activated by blue light, while Halorhodopsin (NpHR) is a chloride pump that when exposed to yellow light hyperpolarizes the cell. For in vitro preparations in the brain, activating light is conventionally delivered with halogen/xenon arc lamps and LEDs, with pulses generated via fast shutter or intensity modulation. In vivo light delivery is more complicated; superficial stimulation relying on small mounted LEDs above the brain, and optical fibers used to target deeper structures.

Distributed structures can thus be more easily interrogated in vitro than in vivo. For example, inhibition of pathologic activity in a slice model of hippocampal epilepsy allows for control of pyramidal neurons across the slice, and our own experiments in the hippocampus with AAV2-CaMKIIa-ChR2 have shown similar results. However experiments in an awake, behaving Parkinson's disease model using optical fibers to direct light indicate that only approximately 0.7 mm$^3$ of tissue can be controlled in this fashion. Thus there is a need for distributed activation of opsins in vivo.

Bioluminescence from luciferase proteins offers an alternative light source for activation of opsins. Bioluminescence from luciferase proteins can be utilized to activate opsins. Coupling the expression of luciferase with opsin in neurons obviates the need for external light sources delivered through implanted optical fibers in vivo and facilitate clinical translation.

Activity-dependent luciferases couple to opsins may be achieved in several ways. Several calcium-sensing luciferases have been developed and used as bioluminescent reporters of neural activity (e.g. GFP-Aequorin, Nanolantern-Ca's). These reagents can be directly utilized to report neural activity in the form of bioluminescence and autonomously activate coupled opsins. One can express luciferase in an activity-dependent fashion. For example, When luciferase expression is driven by an immediate-early gene (c-fos) reporter, they can effectively reflect neuron activity. One illustration of how activity-dependent luminescence could be used to autonomously activate opsins could therefore be rats rendered epileptic with focal injections of tetanus toxin to the hippocampus may be simultaneously infected with viral vectors encoding activity-dependent luciferase (either Ca-sensing or c-fos driven expression), and CaMKIIa-eNpHR. Overactivation of hippocampal neurons due to epileptiform activity would drive bioluminescence, which will then drive bioluminescence of those same neurons through activation of eNpHR, reducing their activity. Hyperpolarization will then bring luciferase activity back toward baseline reducing inhibitory current. This should lead to a steady-state situation, which will reduce pathologic activity and seizures.

Examples

Bioluminescent Resonance Energy Transfer (BRET) Based Reporter

BRET-based reporters are fusion proteins of a luciferase and a fluorescent protein; this fusion allows energy to be transferred from the luciferase to the fluorescent protein, enabling enhanced emission of bright light. Dragulescu-Andrasi et al. report a BRET systems consist of *Renilla* reniformis luciferase (RLuc) variants RLuc8 and RLuc8.6, used as BRET donors, combined with two red fluorescent proteins, TagRFP and TurboFP635, as BRET acceptors. Proc Natl Acad Sci USA, 2011, 108(29):12060-5.

A number of AAV and lentivirus-based vectors have been produced and tested for delivering optogenetic channels. Using viral vectors one can deliver a high copy number of transgene as well as allow cell-type specific expression in in vivo studies. One can transduce luciferase into primary cortical neurons, confirm transgene expression using fluorescence microscopy, and perform a titration experiment with coelenterazine substrate to determine the optimal parameters for producing bioluminescence. AAV encoding eNpHR3.0 and Arch under the control of the CAMKII promoter have been produced.

One delivers luciferase and inhibitory opsin to various primary cortical neuron cultures using the viral vectors. The viral titers used in these co-infections are varied to obtain a heterogeneous population of luciferase-expressing and opsin-expressing cells. Luciferase-expressing cells and opsin-expressing cells are identified by fluorescence microscopy. Coelenterazine substrate is added to the culture in various concentrations, and its effect on network activity is determined.

Simultaneous patch clamp studies are conducted to determine cellular responses in (1) cells expressing both opsin and luciferase (i.e. both components in cis) and (2) cells expressing only opsin (i.e. both components in trans). As an alternative to co-infection, one can also deliver luciferase and inhibitory opsin together as a fusion protein. Various molecular strategies can also be employed (such as adding dimerizing or transmembrane domains) to facilitate co-localization of the luciferase and inhibitory opsin to the cell membrane.

A BRET-based Auto-luminescent Calcium (BRAC) indicator as an bioluminescent reporter is used for several reasons: (1) BRAC has an emission spectrum (peak 530 nm) that overlaps closely with our inhibitory opsins; (2) BRAC has been shown to regenerate faster than other calcium indicators; (3) and BRAC exhibits resonance energy transfer, which produces robust bioluminescent signal. An alternative calcium-sensitive luciferase that can be used as a sensor for neural activity is GFP-aequorin or Nanolantern-Ca.

An exemplary BRET luciferase polypeptide is TagRF-PRluc has SEQ ID NO: 1, MVSKGEELIKENMHMK-LYMEGTVNNHEIFKCTSEGEGKPYEGTQTM-RIKVVEGGPLPFA FDILATSFMYGSRTFINHTQ-GIPDFFKQSFPEGFTWERVTTYEDGGVLTATQDT-SLQDGC LIYNVKIR-GVNFPSNGPVMQKKTLGWEANTEMLYPADGGLEG RSDMALKLVGGGHLIC NFKTTYR-SKKPAKNLKMPGVYYVDHRLERIKEAD-KETYVEQHEVAVARYCDLPSKLG HKLNSGLRS-DIGPSRATMASKVYDPEQRKRMITGPQWWARCKQ MNVLDSFINYYDSEK HAENAVIFLHGNATS-SYLWRHVVPHIEPVARCIIPDLIGMGKSGKSGNG-SYRLLDHYKY LTAWFELLNLPK-KIIFVGHDWGSALAFHYAYEHQDRIKAIVHMESVV DVIESWMGWPDI EEELALIK-SEEGEKMVLENNFFVETLLPSKIMRKLEPEEFAAY-LEPFKEKGEVRRPTLSWP REIPLVKGGKPDVVQI-VRNYNAYLRASDDLPKLFIESDPGFFSNAIVEGAK KFPNTEFVK VKGLHFLQEDAP-DEMGKYIKSFVERVLKNEQ.

An exemplary nucleic acid encoding a BRET luciferase polypeptide has SEQ ID NO: 2, ATGGTGTCTAAGGGCGAAGAGCTGAT-TAAGGAGAACATGCACATGAAGCTGTACAT GGAGGGCACCGTGAACAACCACCACTT-CAAGTGCACATCCGAGGGCGAAGGCAAGC CCTACGAGGGCACCCAGACCATGAGAAT-CAAGGTGGTCGAGGGCGGCCCTCTCCCC TTCGCCTTCGACATCCTGGCTACCAGCTT-CATGTACGGCAGCAGAACCTTCATCAAC CACACCCAGGGCATCCCCGACTTCTT-TAAGCAGTCCTTCCCTGAGGGCTTCACATGG GAGAGAGTCACCACATACGAA-GACGGGGGCGTGCTGACCGC-TACCCAGGACACCAG CCTCCAGGACGGCTGCCT-CATCTACAACGTCAAGATCAGAGGGGTGAACTTCC-CATC CAACGGCCCTGT-GATGCAGAAGAAAACACTCGGCTGGGAGGC-CAACACCGAGATGC TGTACCCCGCTGACGGCGGCCTG-GAAGGCAGAAGCGACATGGCCCTGAAGCTCGTG GGCGGGGGCCACCTGATCTGCAACTTCAAGACCA-CATACAGATCCAAGAAACCCGC TAAGAACCTCAA-GATGCCCGGCGTCTACTATGTGGACCACAGACTG-GAAAGAATCA AGGAGGCCGACAAAGAGACC-TACGTCGAGCAGCACGAGGTGGCTGTGGCCAGATA CTGCGACCTCCCTAGCAAACTGGGGCACAAACT-TAATTCCGGACTCAGATCTGATAT CGGGCCCTCTAGAGCCACCATGGCTTC-CAAGGTGTACGACCCCGAGCAACGCAAAC GCAT-GAT-CACTGGGCCTCAGTGGTGGGCTCGCTGCAAGCA AATGAACGTGCTGGAC TCCTTCATCAACTACTAT-GATTCCGAGAAGCACGCCGAGAACGCCGTGAT-TTTTCTG CATGGTAACGCTACCTCCAGC-TACCTGTGGAGGCACGTCGTGCCTCACATCGA GCCC GTGGCTAGATGCATCATCCCTGATCTGATCG-GAATGGGTAAGTCCGGCAAGAGCGG GAATGGCT-CATATCGCCTCCTGGATCACTACAAGTACCT-CACCGCTTGGTTCGAGCT GCTGAACCTTCCAAAGAAAATCATCTTTGTGGGC-CACGACTGGGGGAGCGCTCTGGC CTTTCAC-TACGCCTACGAGCACCAAGACAGGATCAAGGC-CATCGTCCATATGGAGA GTGTCGTGGACGTGATCGAGTCCTG-GATGGGGTGGCCTGACATCGAGGAGGAGCTG GCCCTGAT-CAAGAGCGAAGAGGGCGAGAAAATGGTGCTT-GAGAATAACTTCTTCGT CGAGACCCTGTTGC-CAAGCAAGATCATGCGGAAACTGGAGCCTGAGG AGTTCGCTG CCTACCTGGAGCCATT-CAAGGAGAAGGGCGAGGTTAGACGGCC-TACCCTCTCCTGG CCTCGCGAGATCCCTCTCGT-TAAGGGAGGCAAGCCCGACGTCGTCCAGATTGT CCGC AACTACAACGCCTACCTTCGGGCCAGCGAC-GATCTGCCTAAGCTGTTCATCGAGTCC GACCCTGGGTTCTTTTCCAACGCTATTGTCGAGG-GAGCTAAGAAGTTCCCTAACACC GAGTTCGT-GAAGGTGAAGGGCCTCCACTTCCTCCAG-GAGGACGCTCCAGATGAAAT GGGTAAGTACATCAAGAGCTTCGTG-GAGCGCGTGCTGAAGAACGAGCAG An exemplary nucleic acid encoding a light-activated opsin is "eNphR3.0-TagRFPRluc" which has SEQ ID NO:3,ATGACAGA-
GACCCTGCCTCCCGTGACCGAGAGTGCCGTGGC
CCTTCAAGCCGAGGTTACCCAAAGG-
GAGTTGTTCGAGTTCGTGCTGAACGACCCTTTGC
TTGCAAGCAGTCTCTATATCAA-
CATCGCACTTGCAGGACT-
GAGTATACTGCTGTTCGTTTTTATGACCCGA
GGACTCGATGATCCACGGGCAAAACTTAT-
TGCTGTGTCAACCATCCTTGTGCCTGTCGTCAG-
CATTGCCTCCTACACTGGAT-
TGGCGAGCGGCCTGACAATTTCCGTTCTTGAA
ATGCCAGCGGGCCAT-
TTTGCAGAAGGCAGCTCAGTGATGCTGGGAG-
GAGAAGAGGTAGATGGTGTAGTCAC-
CATGTGGGGACGGTATCTCACCTGGGCACTTTCC
ACGCCCATGAT-
TCTCCTCGCTCTGGGTCTCCTGGCCG-
GAAGCAATGCTACAAAGCTCTTCACAGC TAT-
CACTTTCGATATCGCTATGTGCGTGACTGGCCTTG
CCGCGGCCCTGACTACCTCCTCCCACCTCAT-
GAGATGGTTCTGGTACGCTATCAGTTGTG-
CATGCTTTCTGGTGGTCTTGTATATCCTGCTGGTG-
GAGTGGGCACAGGACGCCAAAGCCGCGGGAACC
GCTGACATGTTCAATACCCT-
GAAGCTGTTGACAGTAGTGATGTGGCTGGGGTATC-
CAATTGTGTGGGCTCTTG-
GAGTCGAGGGTATCGCGGTGTTGCCCGTTGGGGT
GACGAGCTGGGGATATTCTTTCCTGGA-
TATCGTGGCAAAGTACATTTTCGCATTCTTGCTCCT-
GAACTATCTGACGT-
CAAACGAATCTGTCGTGTCCGGCAGCATTTTGGA
TGTTCCATCTGCTTCTGGGACCCCGGCTGAT-
GATGCGGCCGCTATGGTGTCTAAGGGCAAGAGCT-
GATTAAG GAGAACATGCACATGAAGCTGTACATG-
GAGGGCACCGTGAACAACCACCACTTCAA
GTGCACATCCGAGGGCGAAGGCAAGCCC-
TACGAGGGCACCCAGACCATGAGAATCA
AGGTGGTCGAGGGCGGCCCTCTCCCCTTCGCCTT
CGACATCCTGGCTACCAGCTTCA
TGTACGGCAGCAGAACCTTCATCAAC-
CACACCCAGGGCATCCCCGACTTCTTTAAGC
AGTCCTTCCCTGAGGGCTTCACATGGGAGAGAGT-
CACCACATACGAAGACGGGGGC GTGCTGACCGC-
TACCCAGGACACCAGCCTCCAGGACGGCTGCCT-
CATCTACAACGTC
AAGATCAGAGGGGTGAACTTCCCATC-
CAACGGCCCTGTGATGCAGAAGAAAACACT
CGGCTGGGAGGC-
CAACACCGAGATGCTGTACCCCGCTGACGGCGGC
CTGGAAGGCAGAAGCGACATGGCCCT-
GAAGCTCGTGGGCGGGGCCACCT-
GATCTGCAACTTCAAGACCACATACAGATC-
CAAGAAACCCGCTAAGAACCTCAAGATGCCCGG
CGTCTACTATGTGGACCACAGACTGGAAAGAAT-
CAAGGAGGCCGACAAAGAGACCTACGTCGAG
CAGCACGAGGTGGCTGTGGCCAGA-
TACTGCGACCTCCCTAGCAAACTGGGGCACAA
ACTTAATTCCGGACTCAGATCTGA-
TATCGGGCCCTCTAGAGCCACCATGGCTTCCAA
GGTGTACGACCCCGAGCAACGCAAACGCATGAT-
CACTGGGCCTCAGTGGTGGGCTC
GCTGCAAGCAAATGAACGTGCTGGACTCCTTCAT-
CAACTACTATGATTCCGAGAAGC
ACGCCGAGAACGCCGTGATTTTTCTG-
CATGGTAACGCTACCTCCAGCTACCTGTGGA
GGCACGTCGTGCCTCACATCGAGCCCGTGGCTA-
GATGCATCATCCCTGATCTGATCG
GAATGGGTAAGTCCGGCAAGAGCGGGAATGGCT-
CATATCGCCTCCTGGATCACTACAAGTACCT-
CACCGCTTGGTTCGAGCTGCTGAACCTTC-
CAAAGAAAATCATCTTTGTG
GGCCACGACTGGGGGAGCGCTCTGGCCTTTCAC-
TACGCCTACGAGCACCAAGACAGGATCAAGGC-
CATCGTCCATATGGAGAGTGTCGTGGACGT-
GATCGAGTCCTGGATGG
GGTGGCCTGACATCGAGGAGGAGCTGGCCCTGAT-
CAAGAGCGAAGAGGGCGAGAAAATGGTGCTT-
GAGAATAACTTCTTCGTCGAGACCCTGTTGC-
CAAGCAAGATCATGCG
GAAACTGGAGCCTGAGGAGTTCGCTGCCTACCTG-
GAGCCATTCAAGGAGAAGGGCGAGGTTA-
GACGGCC-
TACCCTCTCCTGGCCTCGCGAGATCCCTCTCGTTA
AGGGAGGCAAGCCCGACGTCGTCCAGAT-
TGTCCGCAACTACAACGCC-
TACCTTCGGGCCAGCGACGATCTGCCTAAGCTGTT-
CATCGAGTCCGACCCTGGGTTCTTTTCCAACGCTAT-
TGTCGA
GGGGAGCTAAGAAGTTCCCTAACACCGAGTTCGT-
GAAGGTGAAGGGCCTCCACTTCCTCCAG-
GAGGACGCTCCAGATGAAATGGGTAAGTACAT-
CAAGAGCTTCGTGGAGCGCG
TGCTGAAGAACGAGCAGTAA.

An exemplary lentiviral vector is plenti-FU-eNphR3.0-TagRFP-Rluc-WPRE (See Lois et al., Germline transmission and tissue-specific expression of transgenes delivered by lentiviral vectors, 2002, Science, 295(5556):868-72) which has SEQ ID NO: 4, (hUB promoter: 2618-3846 and eNphR3.0-TagRFPRluc: 3863-643) GTCGACGGATCGG-
GAGATCTCCCGATCCCCTATGGTGCACTCTCAGTA-
CAATCTGCTCTGATGCCGCATAGT-
TAAGCCAGTATCTGCTCCCTGCTTGTGTGTTGGA
GGTCGCTGAGTAGTGCGCGAGCAAAATTTAAGC-
TACAACAAGGCAAGGCTTGACCGACAATTGC
ATGAAGAATCTGCTTAGGGT-
TAGGCGTTTTGCGCTGCTTCGC-
GATGTACGGGCCAGA TATACGCGTTGACATTGATT-
ATTGACTAGTTATTAATAGTAATCAATTACGGGGTCA
TTAGTTCATAGCCCATATATGGAGTTCCGCGTTA-
CATAACTTACGGTAAATGGCCCG
CCTGGCTGACCGCCCAACGACCCCCGCCCAT-
TGACGTCAATAATGACGTATGTTCCC
ATAGTAACGCCAATAGGGACTTTCCATTGACGT-
CAATGGGTGGAGTATTTACGGTAAACTGCC-
CACTTGGCAGTACATCAAGTGTATCATATGC-
CAAGTACGCCCCCTATTGAC
GTCAATGACGGTAAATGGCCCGCCTGGCAT-
TATGCCCAGTACATGACCTTATGGGACTTTCC-
TACTTGGCAGTACATCTACGTATTAGTCATCGCTAT-
TACCATGGTGATGCGGT
TTTGGCAGTACATCAATGGGCGTGGA-
TAGCGGTTTGACTCACGGGGATTTCCAAGTC
TCCACCCCATTGACGTCAATGG-
GAGTTTGTTTTGGCACCAAAATCAACGGGACTTTC
CAAAATGTCGTAACAACTCCGCCCCAT-
TGACGCAAATGGGCGGTAGGCGTGTACGGTGG-
GAGGTC-
TATATAAGCAGCGCGTTTTGCCTGTACTGGGTCTC
TCTGGTTAGACCAGATCTGAGCCTGG-
GAGCTCTCTGGCTAACTAGGGAACCCACTGCT-
TAAGCCTCAATAAAGCTTGCCTTGAGTGCTT-
CAAGTAGTGTGTGCCCGTCTGTTGTGTGACTCTG GTAACTAGAGATCCCTCAGACCCTTTAGTCAGTGTG-
GAAAATCTCTAGCAGTGGCGCCCGA
ACAGGGACTTGAAAGCGAAAGGGAAACCAGAG-
GAGCTCTCTCGACGCAGGACTCGGCTTGCT-
GAAGCGCGCACGGCAAGAGGCGAGGGGCGGCG
ACTGGTGAGTACGCCAAAAATTTTGACTAGCG-
GAGGCTAGAAGGAGAGAGATGGGTGCGAGAGCG
TCAGTAT TAAGCGGGGAGAATTAGATCGCGATGG-
GAAAAAATTCGGTTAAGGCCAGGGGGA
AAGAAAAAATATAAATTAAAA-
CATATAGTATGGGCAAGCAGGGAGCTAGAACGATT
CGCAGTTAATCCTGGCCTGTTAGAAA-
CATCAGAAGGCTGTAGACAAATACTGGGAC AGC-
TACAACCATCCCTTCAGACAGGATCAGAAGAACT-
TAGATCATTATATAATACAG
TAGCAACCCTCTATTGTGTGCATCAAAGGA-
TAGAGATAAAAGACACCAAGGAAGCT TTAGACAA-
GATAGAGGAAGAGCAAAACAAAAGTAAGAC-
CACCGCACAGCAAGCGG
CCGCTGATCTTCAGACCTGGAGGAGGAGATAT-
GAGGGACAATTGGAGAAGTGAATT
ATATAAATATAAAGTAGTAAAAATTGAACCATTAG-
GAGTAGCACCCACCAAGGCAA
AGAGAAGAGTGGTGCAGAGAGAAAAAGAGCA
GTGGGAATAGGAGCTTTGTTCCTT GGGTTCTTGG-
GAGCAGCAGGAAGCACTATGGGCGCAGCGT-
CAATGACGCTGACGGT ACAGGCCAGACAATTAT-
TGTCTGGTATAGTGCAGCAGCAGAACAATTTGCT
GAGGGCTATTGAGGCGCAACAG-
CATCTGTTGCAACTCACAGTCTGGGGCAT-
CAAGCAGCTCCAGGCAAGAATCCTGGCTGTG-
GAAAGATACCTAAAGGATCAACAGCTCCTGGGA
TTTGGGGTTGCTCTGGAAAACTCATTTGCAC-
CACTGCTGTGCCTTGGAATGCTAGTTGG
AGTAATAAATCTCTGGAACAGATTTGGAAT-
CACACGACCTGGATGGAGTGGGACAG AGAAAT-
TAACAATTACACAAGCTTAATACACTCCTTAATT-
GAAGAATCGCAAAACC
AGCAAGAAAAGAATGAACAAGAATTATTG-
GAATTAGATAAATGGGCAAGTTTGTGG AATTGGTT-
TAACATAACAAATTGGCTGTGGTATATAAAATTATT-
CATAATGATAGTA
GGAGGCTTGGTAGGTT-
TAAGAATAGTTTTTGCTGTACTTTCTATAGT-
GAATAGAGTTAGGCAGGGATATTCACCAT-
TATCGTTTCAGACCCACCTCCCAACCCCGAGGGG
ACCC
GACAGGCCCGAAGGAATAGAAGAAGAAGGTG-
GAGAGAGAGACAGAGACAGATCCA TTCGATTAGT-
GAACGGATCGGCACTGCGTGCGCCAATTCTGCA-
GACAAATGGCAGTA
TTCATCCACAATTTTAAAAGAAAAGGGGGAT-
TGGGGGGTACAGTGCAGGGAAAG AATAGTAGA-
CATAATAGCAACAGACATACAAACTAAAGAATTA-
CAAAAACAAATTA
CAAAAATTCAAAATTTTCGGGTTTATTA-
CAGGGACAGCAGAGATCCAGTTTGGTTAA
TTAAGGGTGCAGCGGCCTCCGCGCCGGGTTTTGG
CGCCTCCCGCGGGCGCCCCCTC
CTCACGGCGAGCGCTGCCACGTCA-
GACGAAGGGCGCAGGAGGCGTTCCTGATCCTTC
CGCCCGGACGCTCAGGACAGCGGCCCGCTGCT-
CATAAGACTCGGCCTTAGAACCCC
AGTATCAGCAGAAGGACATTT-
TAGGACGGGACTTGGGTGACTCTAGGGCACTG
GTTTTCTTTCCAGAGAGCGGAACAGGCGAG- GAAAAGTAGTCCCTTCTCGGCGATTCTGCG GAGG-
GATCTCCGTGGGGCGGTGAACGCCGATGAT-
TATATAAGGACGCGCCGGGTGT
GGCACAGCTAGTTCCGTCGCAGCCGGGAT-
TTGGGTCGCGGTTCTTGTTTGTGGATCGCTGT-
GATCGTCACTTGGT-
GAGTTGCGGGCTGCTGGGCTGGCCGGGGCTTTC
GTGGCCGCCGGGCCGCTCGGTGGGACG-
GAAGCGTGTGGAGAGACCGC-
CAAGGGCTGTAGTCT
GGGTCCGCGAGCAAGGTTGCCCT-
GAACTGGGGGTTGGGGGGAGCGCACAAAATGGC
GGCTGTTCCCGAGTCTTGAATGGAA-
GACGCTTGTAAGGCGGGCTGTGAGGTCGTTGA
AACAAGGTGGGGGG-
CATGGTGGGCGGCAAGAACCCAAGGTCTT-
GAGGCCTTCGCTAATGCGGGAAAGCTCTTAT-
TCGGGTGAGATGGGCTGGGGCACCATCTGGGGA
CCCTGACGTGAAGTTTGTCACTGACTG-
GAGAACTCGGGTTTGTCGTCTGGTTGCGGGGCGG
CAGT-
TATGCGGTGCCGTTGGGCAGTGCACCCGTACCT
TGGGAGCGCGCGCCTCGTCGTGTCGTGACGT-
CACCCGTTCTGTTGGCTTATAATGCAGGGTGGGGC-
CACCTGCCGG
TAGGTGTGCGGTAGGCTTTTCTCCGTCGCAGGA
CGCAGGGTTCGGGCCTAGGGTAGGCTCTCCT-
GAATCGACAGGCGCCGGACCTCTGGTGAGGG-
GAGGGATAAGTGAGGCGT
CAGTTTCTTTGGTCGGTTTTATGTACCTATCTTCT-
TAAGTAGCTGAAGCTCCGGTTTTGAAC-
TATGCGCTCGGGGTTGGCGAGTGTGTTTTGT-
GAAGTTTTTTAGGCACCTTTTGA
AATGTAATCATTTGGGTCAATATGTAAT-
TTTCAGTGTTAGACTAGTAAAGCTTCTGC
AGGTCGACTCTAGAAAATTGTCCGCTAAAT-
TCTGGCCGTTTTTGGCTTTTTTGTTAGACAG-
GATCCCCGGGTACCATGACAGA-
GACCCTGCCTCCCGTGACCGAGAGTGCCGTG
GCCCTTCAAGCCGAGGTTACCCAAAGG-
GAGTTGTTCGAGTTCGTGCTGAACGACCCT
TTGCTTGCAAGCAGTCTCTATATCAA-
CATCGCACTTGCAGGACTGAGTATACTGCTG
TTCGTTTTTATGACCCGAGGACTCGATGATC-
CACGGGCAAAACTTATTGCTGTGTCA
ACCATCCTTGTGCCTGTCGTCAGCATTGCCTCCTA-
CACTGGATTGGCGAGCGGCCTGACAAT-
TTCCGTTCTTGAAATGCCAGCGGGCCAT-
TTTGCAGAAGGCAGCTCAGTGATG
CTGGGAGGAGAAGAGGTAGATGGTGTAGTCAC-
CATGTGGGGACGGTATCTCACCTGGGCACTTTC-
CACGCCCATGAT-
TCTCCTCGCTCTGGGTCTCCTGGCCGGAAGCAATGC
TACAAAGCTCTTCACAGCTATCACTTTCGATATCGC-
TATGTGCGTGACTGGCCTTGCCGCGGCCCTGAC-
TACCTCCTCCCACCTCAT-
GAGATGGTTCTGGTACGCTATCAGTTGT
GCATGCTTTCTGGTGGTCTTGTATATCCTGCTGGTG-
GAGTGGGCACAGGACGCCAAAGCCGCGG-
GAACCGCTGACATGTTCAATACCCT-
GAAGCTGTTGACAGTAGTGATGTGG
CTGGGGTATCCAATTGTGTGGGCTCTTG-
GAGTCGAGGGTATCGCGGTGTTGCCCGTT
GGGGTGACGAGCTGGGATATTCTTTCCTGGA-
TATCGTGCAAAGTACATTTTCGCA TTCTTGCTCCT-
GAACTATCTGACGT-
CAAACGAATCTGTCGTGTCCGGCAGCATTTTGG
ATGTTCCATCTGCTTCTGGGACCCCGGCTGAT-
GATGCGGCCGCTATGGTGTCTAAGG
GCGAAGAGCTGATTAAGGAGAACATGCACAT- GAAGCTGTACATGGAGGGCACCGTG AACAACCAC-
CACTTCAAGTGCA-
CATCCGAGGGCGAAGGCAAGCCCTACGAGGGCAC
CCAGACCATGAGAAT-
CAAGGTGGTCGAGGGCGGCCCTCTCCCCTTCGC
CTTCGACATCCTGGCTACCAGCTT-
CATGTACGGCAGCAGAACCTTCATCAAC-
CACACCCAGGGCATCCCCGACTTCTT-
TAAGCAGTCCTTCCCTGAGGGCTTCACATGGGA
GAGAGTCACCACATACGAA-
GACGGGGGCGTGCTGACCGC-
TACCCAGGACACCAGCCTCCAGGACGGCTGCCT-
CATCTACAACGTCAAGATCAGAGGGGTGAACTTCC-
CATCCAACGGCCCTGTGA
TGCAGAAGAAAACACTCGGCTGGGAGGC-
CAACACCGAGATGCTGTACCCCGCTGAC
GGCGGCCTGGAAGGCAGAAGCGACATGGCCCT-
GAAGCTCGTGGGCGGGGGCCACCT
GATCTGCAACTTCAAGACCACATACAGATC-
CAAGAAACCCGCTAAGAACCTCAAGA
TGCCCGGCGTCTACTATGTGGACCACAGACTG-
GAAAGAATCAAGGAGGCCGACAAA GAGACC-
TACGTCGAGCAGCACGAGGTGGCTGTGGCCAGA-
TACTGCGACCTCCCTAG
CAAACTGGGGCACAAACTTAATTCCGGACTCA-
GATCTGATATCGGGCCCTCTAGAGCCAC-
CATGGCTTC-
CAAGGTGTACGACCCCGAGCAACGCAAACGCA
TGATCACTGGGC
CTCAGTGGTGGGCTCGCTGCAAGCAAAT-
GAACGTGCTGGACTCCTTCATCAACTACT ATGAT-
TCCGAGAAGCACGCCGAGAACGCCGTGAT-
TTTTCTGCATGGTAACGCTACCT
CCAGCTACCTGTGGAGGCACGTCGTGCCTCA-
CATCGAGCCCGTGGCTAGATGCATCATCCCTGATCT-
GATCGGAATGGGTAAGTCCGGCAAGAGCGG-
GAATGGCTCATATCGC
CTCCTGGATCACTACAAGTACCT-
CACCGCTTGGTTCGAGCTGCTGAACCTTCCAAAG
AAAATCATCTTTGTGGGCCACGACTGGGG-
GAGCGCTCTGGCCTTTCACTACGCCTAC GAGCAC-
CAAGACAGGATCAAGGCCCATCGTCCATATG-
GAGAGTGTCGTGGACGTGAT
CGAGTCCTGGATGGGGTGGCCTGACATCGAGGAG-
GAGCTGGCCCTGATCAAGAGCG
AAGAGGGCGAGAAAATGGTGCTT-
GAGAATAACTTCTTCGTCGAGACCCTGTTGCCA
AGCAAGATCATGCGGAAACTGGAGCCTGAG-
GAGTTCGCTGCCTACCTGGAGCCATT
CAAGGAGAAGGGCGAGGTTAGACGGCC-
TACCCTCTCCTGGCCTCGCGAGATCCCTC TCGT-
TAAGGGAGGCAAGCCCGACGTCGTCCAGAT-
TGTCCGCAACTACAACGCCTAC
CTTCGGGCCAGCGACGATCTGCCTAAGCTGTT-
CATCGAGTCCGACCCTGGGTTCTTTT CCAACGCT-
ATTGTCGAGG-
GAGCTAAGAAGTTCCCTAACACCGAGTTCGTGA
AGGTGAAGGGCCTCCACTTCCTCCAG-
GAGGACGCTCCAGATGAAATGGGTAAGTACATCAA
GAGCTTCGTGGAGCGCGTGCT-
GAAGAACGAGCAGTAAGAATTCGATATCAAGCTTA
TCGATAATCAACTCTGGATTACAAAATTTGT-
GAAAGATTGACTGGTATTCTTAACT
ATGTTGCTCCTTTTACGCTATGTGGATACGCTGCTT-
TAATGCCTTTGTATCATGCTAT
TGCTTCCCGTATGGCTTTCAT-
TTTCTCCTCCTTGTATAAATCCTGGTTGCTGTCT CTTTATGAG-
GAGTTGTGGCCCGTTGTCAGGCAACGTGGCGTG
GTGTGCACTGTGTTTGCTGACGCAACCCC-
CACTGGTTGGGGCATTGCCAC-
CACCTGTCAGCTCCTTTCCGGGACTT
TCGCTTTCCCCCTCCCTATTGCCACGGCGGAACT-
CATCGCCGCCTGCCTTGCCCGCTG
CTGGACAGGGGCTCGGCTGTTGGGCACTGACAAT-
TCCGTGGTGTTGTCGGGGAAATC
ATCGTCCTTTCCTTGGCTGCTCGCCTGTGTTGC-
CACCTGGATTCTGCGCGGGACGTCCTTCTGC-
TACGTCCCTTCGGCCCT-
CAATCCAGCGGACCTTCCTTCCCGCGGCCTGCTGC
CGGCTCTGCGGCCTCTTCCGCGTCTTCGCCTTCG
CCCTCAGACGAGTCGGATCTCCCT
TTGGGCCGCCTCCCCGCATCGA-
TACCGTCGACCTCGAGACCTAGAAAAACATGGAG
CAATCACAAGTAGCAATACAGCAGCTACCAATGCT-
GATTGTGCCTGGCTAGAAGCACAAGAGGAGGAG-
GAGGTGGGTTTTCCAGTCACACCTCAGGTACCTT-
TAAGACCAAT
GACTTACAAGGCAGCTGTAGATCTTAGCCACTTTT-
TAAAAGAAAAGGGGGGACTGG AAGGGCTAATT-
CACTCCCAACGAAGACAAGATATCCTTGATCTGTG-
GATCTACCACA
CACAAGGCTACTTCCCTGATTGGCAGAACTA-
CACACCAGGGCCAGGGATCAGATAT
CCACTGACCTTTGGATGGTGCTA-
CAAGCTAGTACCAGTTGAGCAAGAGAAGGTAGA
AGAAGCCAATGAAGGAGAGAACACCCGCTTGTTA-
CACCCTGTGAGCCTGCATGGGA TGGATGACCCG-
GAGAGAGAAGTATTAGAGTG-
GAGGTTTGACAGCCGCCTAGCATTT
CATCACATGGCCCGAGAGCTG-
CATCCGGACTGTACTGGGTCTCTCTGGTTAGACCA-
GATCTGAGCCTGGGAGCTCTCTGGCTAACTAGG-
GAACCCACTGCTT
AAGCCTCAATAAAGCTTGCCTTGAGTGCTT-
CAAGTAGTGTGTGCCCGTCTGTTGTGTGACTCT
GGTAACTAGAGATCCCTCAGACCCTTT-
TAGTCAGTGTGGAAAATCTCTAGCAGGGCCCGTT-
TAAACCCGCT-
GATCAGCCTCGACTGTGCCTTCTAGTT
GCCAGCCATCTGTTGTTTGCCCCT
CCCCCGTGCCTTCCTTGACCCTGGAAGGTGC-
CACTCCCACTGTCCTTTCCTAATAAAATGAG-
GAAATTGCATCGCATTGTCTGAGTAGGTGTCATTCT-
ATTCTGGGGGGTGGGGT
GGGGCAGGACAGCAAGGGGGAGGATTGGGAA-
GACAATAGCAGGCATGCTGGGGAT
GCGGTGGGCTCTATGGCTTCTGAGGCG-
GAAAGAACCAGCTGGGGCTCTAGGGGGTATCCC-
CACGCGCCCTGTAGCGGCGCAT-
TAAGCGCGGCGGGTGTGGTGGTTACGCGCA
GCGTGACCGCTA-
CACTTGCCAGCGCCCTAGCGCCCGCTCCTT
TCGCTTTCTTCCCTTCCTTTCTCGC-
CACGTTCGCCGGCTTTCCCCGT-
CAAGCTCTAAATCGGGGGCTCCCTTTAGGGTTCC-
GATTTAGTGCTTTACGGCACCTCGACCCC
AAAAAACTTGATTAGGGTGATGGTT-
CACGTAGTGGGCCATCGCCCTGATA-
GACGGTTTTTCGCCCTTTGACGTTGGAG
TCCACGTTCTTTAATAGTGGACTCTTGTTC-
CAAACTGGAACAACACTCAACCCTATCT CGGTCT-
ATTCTTTTGATTTATAAGGGATTTTGCCGAT-
TTCGGCCTATTGGTTAAAAAA
TGAGCTGATTTAACAAAAATTTAACGCGAATTAAT-
TCTGTGGAATGTGTGTCAGTTAGGGTGTG GAAAGTCCCCAGGCTCCCCAGCAGGCAGAAGT ATGCAAAGCATGCATCTCAATT-AGTCAGCAACCAGGTGTG-
GAAAGTCCCCAGGCTCCCCAGCAGGCAGAAGTA TGCAAAGCATGCATCTCAATTAGTCAGCAACCAT-AGTCCCGCCCCTAACTCCGCCCA
TCCCGCCCCTAACTCCGCCCAGTTCCGCCCAT-TCTCCGCCCCATGGCTGACTAATTTT TTTTATT-TATGCAGAGGCCGAGGCCGCCTCTGCCTCTGAGCT-ATTCCAGAAGTAGTG
AGGAGGCTTTTTG-GAGGCCTAGGCTTTTGCAAAAAGCTCCCGG-GAGCTTGTATATCCATTTTCGGATCT-GATCAGCACGTGTTGACAATTAATCATCGGCATA GTATATCGGC ATAGTATAATACGACAAGGTGAG-GAACTAAACCATGGCCAAGTTGACCAGTGCCGT TCCGGTGCTCACCGCGCGCGACGTCGCCG-GAGCGGTCGAGTTCTGGACCGACCGGC TCGGGTTCTCCCGGGACTTCGTG-GAGGACGACTTCGCCGGTGTGGTCCGGGACGACG TGACCCTGTT-CATCAGCGCGGTCCAGGACCAGGTGG TGCCGGACAACACCCTGGCCT GGGTGTGGGTGCGCGGCCTGGACGAGC TGTACGCCGAGTGGTCGGAGGTCGTGTCC ACGAACTTCCGGGACGCCTCCGGGCCGGC-CATGACCGAGATCGGCGAGCAGCCGTG GGGGCGG-GAGTTCGCCCTGCGCGACCCGGCCGGCA ACTGCGTGCACTTCGTGGCCG
AGGAGCAGGACTGACACGTGCTACGAGATTTC-GATTCCACCGCCGCCTTCTATGAAA GGTTGGGCTTCG-GAATCGTTTTCCGGGACGCCGGCTGGAT-GATCCTCCAGCGCGGGGATCTCATGCTG-GAGTTCTTCGCCCACCCCAACTTGTTTATTGCAGCT-TATAATGGTTA
CAAATAAAGCAATAGCATCACAAATTT-CACAAATAAAGCATTTTTTTCACTGCATTC TAGTTGTGGTTTGTCCAAACTCATCAATGTATCT-TATCATGTCTGTATACCGTCGACC TCTAGCTAGAGCTTGGCGTAATCATGGTCAT-AGCTGTTTCCTGTGTGAAATTGTTATCCGCT-CACAATTCCACACAACATACGAGCCGGAAGCAT-AAAGTGTAAAGCCTGGGGT GCCTAATGAGTGAGCTAACTCACATTAAT-TGCGTTGCGCTCACTGCCCGCTTTCCAGTCGG-GAAACCTGTCGTGCCAGCTGCATTAATGAATCGGC-CAACGCGCGGGGAGAGG
CGGTTTGCGTATTGGGCGCTCTTCCGCTTCCTCGCT-CACTGACTCGCTGCGCTCGGTC
GTTCGGCTGCGGCGAGCGGTATCAGCTCACT-CAAAGGCGGTAATACGGTTATCCACA GAATCAGGGGATAACGCAGGAAAGAACATGT-GAGCAAAAGGCCAGCAAAAGGCCA GGAACCGTAAAAAGGCCGCGTTGCTGGCGTTTTTC-CATAGGCTCCGCCCCCCTGACGAGCAT-CACAAAAATCGACGCT-CAAGTCAGAGGTGGCGAAACCCGACAGGACTATAA AGATACCAGGCGTTTCCCCCTG-GAAGCTCCCTCGTGCGCTCTCCTGTTCCGACCCTG CCGCTTACCGGA-TACCTGTCCGCCTTTCTCCCTTCGG-GAAGCGTGGCGCTTTCTCATAGCT-CACGCTGTAGGTATCTCAGTTCGGTGTAG GTCGTTCGCTCCAAGCTGGGCTGTG TGCACGAACCCCCCGTTCAGCCCGACC GCTGCGCCTTATCCGGTAACTATCGTCTTGAGTC-CAACCCGGTAAGACACGACTTATCGC-
CACTGGCAGCAGCCACTGGTAACAGG ATTAGCAGAGCGAGGTATGTAGGCGGTGCTA-CAGAGTTCTTGAAGTGGTGGCCTAA CTACGGCTA-CACTAGAAGAACAGTAT-
TTGGTATCTGCGCTCTGCTGAAGCCAGTTAC CTTCGGAAAAAGAGTTGGTAGCTCTT-GATCCGGCAAACAAACCACCGCTGGTAGCG GTGGTTTTTTTGTTTGCAAGCAGCAGAT-TACGCGCAGAAAAAAGGATCTCAAGAA GATCCTTTGATCTTTTC-TACGGGGTCTGACGCTCAGTGGAACGAAAACT-CACGTTAAGGGATTTTGGTCATGAGATTAT-CAAAAAGGATCTTCACCTAGATCCTTTTAAATTAA AAATGAAGTTTTAAATCAATCTAAAGTATATAT-GAGTAAACTTGGTCTGACAGTTACCAATGCT-TAATCAGTGAGGCACCTATCTCAGCGATCTGTCTAT-TTCGTTCATCCATAG
TTGCCTGACTCCCCGTCGTGTAGATAACTACGA-TACGGGAGGGCTTACCATCTGGCC CCAGTGCTGCAATGATACCGCGAGACCCACGCT-CACCGGCTCCAGATTTATCAGCAA TAAACCAGCCAGCCG-GAAGGGCCGAGCGCAGAAGTGGTCCTGCAACTT-TATCCGCC TCCATCCAGTCTATTAATTGTTGCCGG-GAAGCTAGAGTAAGTAGTTCGCCAGTTAAT AGTTTGCGCAACGTTGTTGCCATTGCTACAGG-CATCGTGGTGTCACGCTCGTCGTTTG GTATGGCTT-CATTCAGCTCCGGTTCCCAACGATCAAGGCGAGT-TACATGATCCCCCA
TGTTGTGCAAAAAAGCGGT-TAGCTCCTTCGGTCCTCC-GATCGTTGTCAGAAGTAAGTTGGCCGCAGTGTTAT-CACTCATGGTTATGGCAGCACTGCATA ATTCTCTTACTGTCATGCCATCCGTAA-GATGCTTTTCTGTGACTGGTGAGTACTCAAC-CAAGTCATTCTGAGA
ATAGTGTATGCGGCGACCGAGTTGC TCTTGCCCGGCGTCAATACGGGATAATACCGC GCCACATAGCAGAACTTTAAAAGTGCTCATCATTG-GAAAACGTTCTTCGGGGCGAAAACTCT-CAAGGATCTTACCGCTGTTGAGATCCAGTTC-GATGTAACCCACTCGTGCAC CCAACTGATCTTCAGCATCTTTTACTTT-CACCAGCGTTTCTGGGTGAGCAAAAACAG GAAGGCAAAATGCCGCAAAAAAGG-GAATAAGGGCGACACGGAAATGTTGAATACT CAT-ACTCTTCCTTTTTCAATATTATTGAAGCATT-TATCAGGGTTATTGTCTCATGAGC GGATACATATTTGAATGTATT-TAGAAAAATAAACAAATAGGGGTTCCGCGCA-CATTT CCCCGAAAAGTGCCACCTGAC.

Other exemplary vectors are pAAV-CAMKIIa-eN-phR3.0-Nanolantern (SEQ ID NO: 14) shown in FIG. 7A, plenti-eNphR3.0-Nanolantern (SEQ ID NO: 13) in FIG. 7B, and plenti-eNphR3.0-NL-600 (SEQ ID NO: 12) in FIG. 7C.

The amino acid sequence for the eNpHR3.0-Nanolantern cassette is (SEQ ID NO: 11)
MTETLPPVTESAVALQAEVTQRELFEFVLNDPL-LASSLYINIALAGLSILLFVFMT RGLDDPRAKLIA-VSTILVPVVSIASYTGLASGLTISVLEMPAGHFAE-GSSVMLGGEEVDG
VVTMWGRYLTWALSTPMILLALGLLAG-SNATKLFTAITFDIAMCVTGLAAALTTSSHL MRWFWYAISCACFLVVLYILLVEWAQDA-KAAGTADMFNTLKLLTVVMWLGYPIVWA LGVEGI-AVLPVGVTSWGYSFLDIVAKYIFAFLLLNYLTS-NESVVSGSILDVPSASGTPADD AAAVSKGEELFTGVVPIL-
VELDGDVNGHKFSVSGEGEG-
DATYGKLTLKLICTTGKLPVPWPTLVTTLGYGLQC-
FARYPDHMKQHDFFKSAMPEGYVQERTIFF
KDDGNYKTRAEVKF EGDTLVNRIELKGIDFKEDG-
NILGHKLEYNYNSHNVYITADKQKNGI-
KANFKIRHNIEDGGVQLADHYQQNT-
PIGDGPVLLPDNHYLSYQSKLSKDPNEKRDH
MVLLEFVTAAGGTKVYDPEQRKR-
MITGPQWWARCKQMNVLDSFINYYDSEKHAENAVI-
FLHGNATSSYLWRHVVPHIEPVARCI-
IPDLIGMGKSGKSGNGSYRLLDHYKYL
TAWFELLNLPKKIIFVGHDWG
AALAFHYAYEHQDRIKAIVHMESVVD-
VIESWDEWPDIEEDIALIKSEEGEKMVLENNFF
VETVLPSKIMRKLEPEEFAAYLEPFKEK-
GEVRRPTLSWPREIPLVKGGKPDVVQIVRNYN AYLR-
ASDDLPKLFIEGDPGFFSNAIVEG-
AKKFPNTEFVKVKGLHFLQEDAPDEMGKYIKS
FVERVLKNEQFCYENEV.

Tetracycline Transactivator (tTA) Driven by a c-Fos Promoter

Another approach one can take for activity-dependent luminescence is to temporally define the expression of luciferase during periods of high neural activity. C-fos is an immediate-early gene that has been used as a marker of recent neural activity. One can drive luciferase expression under the control of a c-fos promoter. The presence of Dox inhibits c-fos-promoter-driven tTA from binding to its target tetracycline-responsive element (TRE) site, which in turn prevents it from driving protein expression. See Liu, X. et al. Optogenetic stimulation of a hippocampal engram activates fear memory recall. Nature 484, 381-385, (2012).

One can demonstrate activity-dependent expression of luciferase in dissociated cortical neuron cultures grown on multielectrode arrays (MEAs). Desirable constructs are delivered to cultures using viral vectors such as tetracycline transactivator (tTA) driven by a c-fos promoter and a luciferase driven by the tetracycline regulator element (TRE). In cells expressing both constructs, Doxycycline (Dox) inhibits c-fos driven tTA from binding to its target TRE, which would prevent it from driving expression of the luciferase. In the absence of Dox, luciferase expression can be driven by c-fos activity. Thus, one can define luciferase expression only during periods where Dox is not present and neuronal activity is high.

Activity-dependent luminescence may be assessed by evoking spiking activity in the MEA cultures through electrical stimulation in the presence and absence of doxycycline. Only a subset of contacts in the MEA can be stimulated to produce differential levels of spiking activity throughout the culture. One can see luciferase expression (as determined by fluorescence microscopy) and luminescence (as determined by bioluminescence imaging) when spiking activity is high in the absence of doxycycline. The duration of electrical stimulation and doxycycline removal time may be assessed to determine the optimal conditions for activity-dependent labeling.

This approach may be easily translatable to in vivo models with the use of transgenic c-fos-tTA animals.

In Vivo Evaluation of Optogenetic Inhibition

One stereotactically injects viruses carrying the autonomous biologic controller to the hippocampus of non-epileptic rats. One confirms coexpression of the transgenes in the dorsal hippocampus, characterizes expression levels and determines cell type specificity using histologic methods. In addition, animals are co-infected with the viral vectors, and epilepsy will be induced via stereotactic injection of tetanus toxin to the hippocampus. One examines single-unit and local field potential recordings for evidence of epileptic activity, such as seizures, interictal spikes, and high frequency oscillations. These are correlated with behavioral manifestations of epilepsy, with continuous video recording, as Racine level 5 seizures are common in the tetanus toxin model.

An acute seizure model is intracerebral injection of 4-aminopyridine or bicuculline.

The invention claimed is:

1. A recombinant protein comprising the amino acid sequence of SEQ ID NO: 11.

2. An isolated nucleic acid encoding a recombinant protein comprising the amino acid sequence of SEQ ID NO: 11.

3. An isolated vector comprising a nucleic acid encoding a recombinant protein comprising the amino acid sequence of SEQ ID NO: 11.

4. The isolated vector of claim 3 which is a lentivirus.

5. The isolated vector of claim 3 which is an adenovirus or adeno-associated virus (AAV).

6. The isolated vector of claim 3 which is a retrovirus.

7. The isolated vector of claim 3 which is a vaccinia virus.

8. The isolated vector of claim 3 which is a poxvirus.

9. The isolated vector of claim 3 which is a herpes simplex virus.

10. The isolated vector of claim 3 further encoding tetracycline transactivator (rtTA).

11. The isolated vector of claim 3 further comprising a c-fos promoter.

12. The isolated vector of claim 3 further comprising a tetracycline regulator element (TRE).

13. An in vitro expression system comprising the isolated vector of claim 3.

14. An isolated host cell comprising the isolated vector of claim 3.

* * * * *